United States Patent
Munnes et al.

(10) Patent No.: US 10,155,950 B2
(45) Date of Patent: Dec. 18, 2018

(54) IMMUNOSTIMULATORY PLASMIDS

(71) Applicant: Bayer Animal Health GmbH, Leverkusen (DE)

(72) Inventors: Marc Munnes, Erkrath (DE); Christian Weiss, Leverkusen (DE); Elisabeth Feldhues, Bergisch Gladbach (DE); Romina G. Schauer, Lenexa, KS (US); Albert Abraham, Shawnee, KS (US); Andrea Eicker, Mochengladbach (DE); Hermann Wehlmann, Wuppertal (DE)

(73) Assignee: Bayer Animal Health GmbH, Leverkusen (DE)

( * ) Notice: Subject to any disclaimer, the term of this patent is extended or adjusted under 35 U.S.C. 154(b) by 0 days.

(21) Appl. No.: 14/633,920

(22) Filed: Feb. 27, 2015

(65) Prior Publication Data

US 2015/0267201 A1    Sep. 24, 2015

Related U.S. Application Data

(60) Provisional application No. 61/946,372, filed on Feb. 28, 2014.

(51) Int. Cl.

| | |
|---|---|
| *C07H 21/04* | (2006.01) |
| *A61K 31/70* | (2006.01) |
| *C12N 15/117* | (2010.01) |
| *A61K 39/245* | (2006.01) |
| *A61K 39/108* | (2006.01) |
| *A61K 45/06* | (2006.01) |
| *A61K 9/127* | (2006.01) |
| *A61K 47/54* | (2017.01) |
| *A01K 67/00* | (2006.01) |
| *A61K 39/00* | (2006.01) |

(52) U.S. Cl.
CPC .......... *C12N 15/117* (2013.01); *A61K 9/1272* (2013.01); *A61K 39/0258* (2013.01); *A61K 39/245* (2013.01); *A61K 45/06* (2013.01); *A61K 47/543* (2017.08); *A61K 2039/53* (2013.01); *A61K 2039/54* (2013.01); *A61K 2039/552* (2013.01); *A61K 2039/55555* (2013.01); *A61K 2039/57* (2013.01); *A61K 2039/575* (2013.01); *C12N 2320/31* (2013.01); *C12N 2710/16734* (2013.01); *C12N 2710/16771* (2013.01)

(58) Field of Classification Search
CPC ........ C12N 15/117; C12N 2710/16734; A61K 9/1272; A61K 47/543; A61K 2039/53
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,133,974 A | 7/1992 | Paradissis et al. |
| 5,407,686 A | 4/1995 | Patel et al. |
| 5,427,791 A | 6/1995 | Ahmad et al. |
| 5,736,152 A | 4/1998 | Dunn |
| 5,830,878 A | 11/1998 | Gorman et al. |
| 6,048,535 A | 4/2000 | Sharma |
| 6,207,646 B1 | 3/2001 | Krieg et al. |
| 6,239,116 B1 | 5/2001 | Krieg et al. |
| 6,406,702 B1 | 6/2002 | Sharma |
| 6,429,199 B1 | 8/2002 | Krieg et al. |
| 6,693,086 B1 | 2/2004 | Dow et al. |
| 7,056,492 B2 | 6/2006 | Goudie et al. |
| 2001/0030866 A1 | 10/2001 | Hochstein |
| 2003/0022854 A1 | 1/2003 | Dow et al. |
| 2003/0191082 A1 | 10/2003 | Wheeler |
| 2004/0002472 A1 | 1/2004 | Audonnet et al. |
| 2005/0191342 A1 | 9/2005 | Tam et al. |
| 2006/0223769 A1 | 10/2006 | Dow et al. |
| 2007/0134200 A1 | 6/2007 | Eldridge et al. |
| 2007/0230186 A1 | 10/2007 | Chien |
| 2008/0049399 A1 | 2/2008 | Lu et al. |
| 2009/0263423 A1 | 10/2009 | Fairman et al. |
| 2012/0064151 A1 | 3/2012 | Abraham |
| 2013/0295167 A1 | 11/2013 | Abraham et al. |

FOREIGN PATENT DOCUMENTS

| | | |
|---|---|---|
| CL | 00065 | 1/2011 |
| UY | 33821 A | 7/2012 |
| WO | 9966879 A2 | 12/1999 |
| WO | 2002086101 A2 | 10/2002 |
| WO | 2005079506 A2 | 9/2005 |

(Continued)

OTHER PUBLICATIONS

Yew et al. Reducing the immunostimulatory activity of CpG-containing plasmid DNA vectors for non-viral gene therapy. Expert Opin. Drug Deliv. 1:115-125, 2004.*

Quan et al. Plasmid containing CpG oligodeoxynucleotides can augment the immune responses of pigs immunized with porcine reproductive and respiratory syndrome killed virus vaccine. Veterinary Immunology and Immunopathology 136:257-164, 2010.*

Luo et al. Plasmid DNA containing multiple CpG motifs triggers a strong immune response to hepatitis B surface antigen when combined with incomplete Freund's adjuvant but not aluminum hydroxide. Molecular Medicine Reports 6:1309-1314, 2012.*

Al-Khalaf et al., "Bacterial Contamination of Hatcheries", Journal of Agricultural and Veterinary Sciences, 2010, 2(2), pp. 67-76.

(Continued)

*Primary Examiner* — Quang Nguyen

(57) ABSTRACT

The present invention relates to immunomodulator compositions and methods of use as well as methods of making. The immunomodulator compositions comprise immunostimulatory plasmids, or DNA sequence, capable of eliciting an immune response in a recipient subject. Further, the immunostimulatory plasmids, or DNA sequence, do not contain antibiotic resistance coding sequence to help reduce the potential of horizontal transfer of antibiotic resistance in a population.

20 Claims, 5 Drawing Sheets

Specification includes a Sequence Listing.

(56) References Cited

FOREIGN PATENT DOCUMENTS

| WO | 2005079511 A2 | 9/2005 |
| WO | 2007117303 A2 | 10/2007 |
| WO | 20090120811 A1 | 10/2009 |
| WO | 20100051210 A1 | 5/2010 |
| WO | 2010130374 A1 | 11/2010 |
| WO | 2012084951 A1 | 6/2012 |

OTHER PUBLICATIONS

Angen, O., et al., "Taxonomic relationships of the [Pasteurella] haemolytica complex as evaluated by DNA-DNA hybridizations and 16S rRNA sequencing with proposal of *Mannheimia haemolytica* gen. nov., comb. nov., *Mannheimia granulomatis* comb. nov., *Mannheimia glucosida* sp. nov., *Mannheimia ruminalis* sp. nov. and *Mannheimia varigena* sp. nova," 1999, Int'l J. Systematic Bacteriology, 49:67-86.
Babiuk, L.A., "Broadening the Approaches to Developing More Effective Vaccines," 1999, Vaccine, 1587-1595, 9 pages.
Bryant et al., "Mice, men and the relatives: cross-species studies underpin innate immunity", Open Bioiogy, 2012, 120015, 11 pages.
Buttaro C., et al., "Engineered *E. coli* as Vehicles for Targeted Therapeutics," 2010, Current Gene Therapy, 10:27-33.
Cornelie, J. et al., Methylated CPG-Containing Plasmid Activates the Immune System; Scandinavian Journal of Immunology, 2004, vol. 59, No. 2, pp. 143-151.
Dow, et al., "Lipid-DNA Complexes induce Potent Activation of Innate Immune Responses and Antitumor Activity When Administered Intravenously," 1999, J Immun, 163:1552-1561.
Dow, et al,, "Liposome-Nucleic, Acid Immunotherapeulics," 2008, Expert Opinion Drug Delivery, 5/1: 11-24.
Fasina, Y.O., et al., Influence *Salmonella enterica* Serovar Typhimurium Infection on Intestinal Gobiet Cells and Vilious Morphology in Broiler Chicks; Avian Diseases, (2010), 54, pp. 841-847.
Gomis, S. et al., Protection of Chickens Against *Escherichia coli* Infections by DNA Containing CPG Motifs; Infection and Immunity, (Feb. 2003), vol. 71, No. 2, pp. 857-863.
Gomis, S. et al., Protection of Neonatal Chicks Against a Lethal Challenge of *Escherichia coli* Using DNA Containing Cytosine-Phosphodiester-Guanine Motifs; Avian Diseases. (2004), 48, pp. 813-822.
Gursel, I., et al., Sterically Stabilized Cationic Liposomes Improve the Uptake and Immunostimulatory Activity of CPG Oligonucleotides, Journal of Immunology, 2001, vol. 167, No. 6, pp. 3324-3328.
Haygreen et al., "DNA vaccines for poultry: the jump from theory to practice", Expert Rev Vaccines. Feb. 2005;4(1):51-62.
Krieg Authur M., CPG Motifs in Bacterial DNA and Their Immune Effects*, Annu. Rev. Immunol. 2002, 20:709-760, 54 pages.
Levesque, S., et al., Improvement of Adjuvant Systems to Obtain a Cost-Effective Production of High Levels of Specific IGY; Poultry Science, 2007, vol. 86, No. 5, pp. 630-635.
Mak et al., "Comparative Immunology", The Immune Response, Basic and Clinical Principles, Chapter 21, 2006, pp. 611-637.
Makela Tomi P. et al., Plasmid pLTRpoly: a versatile high-efficiency mammalian expression vector *, Gene. 118 (1992) 293-294, Elsevier Science Publishers B.V., 0378-I 119/92, 2 pages.
Morrey et al., "Efficacy of Cationic Lipid-DNA Complexes (CLDC) on Hepatitis B Virus in Transgenic Mice," 2008, Antiviral Res., 79:71-79.
Nichani, A.K., Subcutaneous, but not Intratracheal Administration of the TLR9 Agonist, CPG DNA Transiently Reduces Parainfluenza-3 Virus Shedding in Newborn Lambs; Comparative Immunology, Microbiology and Infectious Diseases, (2010), 33, pp. E111-E117.
Olsson, B., et al., "Chapter 2 Pulmonary Drug Metabolism, Clearance, and Absorption," 2011, Controlled Pulmonary Drug Delivery, Advances in Delivery Science and Technology, H.D.C. Smyth and A.J. Hickey, Eds., XIV, pp. 21-50.

Patel, B.A., et al., Oligodeoxynucleotides Containing CPG Motifs (CPG-ODN) Predominantly Indue TH1-Type Immune Response in Neonatal Chicks; Developmental and Comparative Immunology, (2008), 32, pp. 1041-1049.
Penha Filho, R.A., et al., Control of *Salmonella enteritidis* and *Salmonella gallinarum* in Birds by Using Live Vaccine Candidate Containing Attenuated *Salmonella gallinarum* Mutant Strain; Vaccine, (2010), 28, pp. 2853-2859.
Pneumonia—Bovine Respiratory Disease—Dairy (BRD), www.zoetis.com.au/diseases/215/pneumonia, downloaded Jan. 24, 2014, 4 pages.
Rice, J. A. et al, "Mannheimia haemolytica and bovine respiratory disease", Animal Health Research Reviews 8(2); 2008, 117-128.
Sambrook, J., et al., Molecular Cloning a Laboratory Manual, Cold Spring Harbor Laboratory Press, (1989), 2nd Ed., pp. 4.22-4.23 & pp. 4.37-4.38.
Sellins et al., "Type I Interferons Potently Suppress Gene Expression Following Gene Delivery Using Liposome-DNA Complexes", Molecular Therapy, 2005, 12(3), pp. 451-459.
Suarez, D.L., et al., "The Effect of Eukaryotic Expression Vectors and Adjuvants on DNA Vaccines in Chickens Using an Avian influenza Model," 2000, Avian Diseases, 44/4:861-868.
Taghavi, A., et al,, Enhancement of Immunoprotective Effect of CPG-ODN by Formulation with Polyphosphazenes Against *E. coli* Septicemia in Neonatal Chickens: Current Drug Delivery, (2009), 6, pp. 76-82.
Taghavi, Azita, "Immunostimulatory effects and delivery of oligodeoxyriucleotides containing CpG motifs (CpG-ODN) in neonatal broiler chickens", Thesis, University of Saskatchewan, Apr. 2008, 175 pages.
Tufan, et al., Save Poultry from *Escherichia coli* Infections, Poultry Punch, 2011, 2811), pp. 58-60.
Vaccine Adjuvants: Preparation Methods and Research Protocols, D. T. O'Hagan, Ed., 2000, Human Press Inc., Totowa, NJ 07512, Chapter 18, "DNA as an Adjuvant", pp. 300-301, XP055136002, 6 pages.
Vandermeulen G. et al., New Generation of Plasmid Backbones Devoid of Antibiotic Resistance Marker for Gene Therapy Trials, The American Society of Gene & Cell Therapy, www.moleculartherapy.org, vol. 19 No. 11, 1942-1949, Nov. 2011, 8 pages.
Verminnen, K. et al., Vaccination of Turkeys Against Chlamydophila Psittaci Through Optimised DNA Formulation and Administration; Vaccine, 2010, vol. 28, No. 18, pp. 3095-3105.
Warner et al., "Recombinant DNA Advisory Committee, Protocol Review #0808-934 and #0808-936," Dec. 3, 2008, 93 pages.
Zaks, et al., "Efficient Immunization and Cross-Priming by Vaccine Adjuvants Containing TLR3 of TLR9 Agonists Complexed to Cationic Liposomes," 2006, J Immunol, 176:7335-7345, 12 pages.
Heyndrickx, M. et al, "Routes for *Salmonella* contamination of poultry meat: epidemiological study from hatchery to slaughterhouse", Epidemiol. Infect. (2002), 129, 253-265.
De Reu, K. et al., "The effect of a commercial UV disinfection system on the bacterial load of shell eggs", The Society of Applied Microbiology, Letters in Applied Microbiology ISSN 0266-8254, 42, 2006, 144-148.
International Preliminary Report on Patentability in Related PCT/EP2011/073414 dated Jun. 26, 2013, 9 pages.
Babiuk, L.A.; et al., Molecular Approaches to Disease Control, Poultry Science Association, Inc., 2003, 82:870-875.
Gomis, S. et al., Protection of chickens against a lethal challenge of *Escherichia coli* by vaccine containing CPT Oligodeoxynucleotides as an adjuvant, Avian Diseases, 2007, 78-83.
Giambrone, J., et al., Vaccinating Eggs? In Ovo Administration of IBDV Vaccines in Broiler Hatching Eggs Shows Promise, Highlights of Agricultural Research, 46:4 (1999), pp. 1-3.
Balazs, D., et al., Review Article Liposomes for Use in Gene Delivery, Journal of Drug Delivery, vol. 2011, 326497, 12 pages.
Peubez, I., et al., Antibiotic-free selection in *E. coli*: new considerations for optimal design and improved production, Microbial Cell Factories 2010, 9:65.
Williams, C., In ovs vaccination for disease prevention, International Poultry Production—vol. 15 No. 8.

(56) References Cited

OTHER PUBLICATIONS

Yamamoto, S., et al., Discovery of Immunostimulatory CpG-DNA and its application to tuberculosis vaccine development, Japanese Journal of Infectious Diseases, 2002, 55(2):37-44.
Yamamoto, S., et al., DNA from Bacteria, but not from Vertebrates Induces Interferons, Activates Natural Killer Cells and Inhibits Tumor Growth; Microbiol. Immunol. vol. 36 (9), 1992, 983-987.
Zhi, D., et al, The Headgroup Evolution of Cationic Lipids for Gene Delivery, Bioconjugate Chem., 2013, 24 (4), pp. 487-519.

* cited by examiner

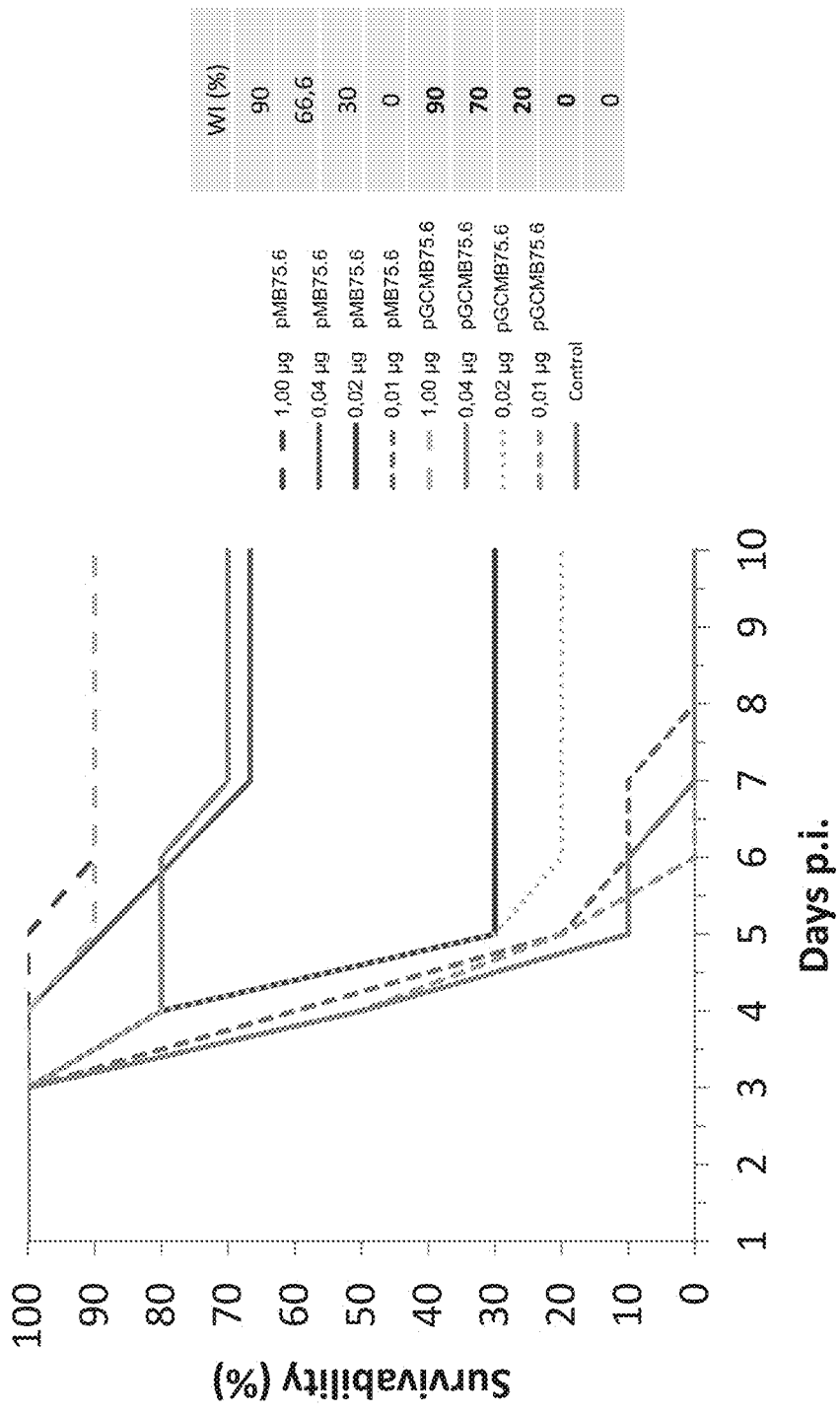

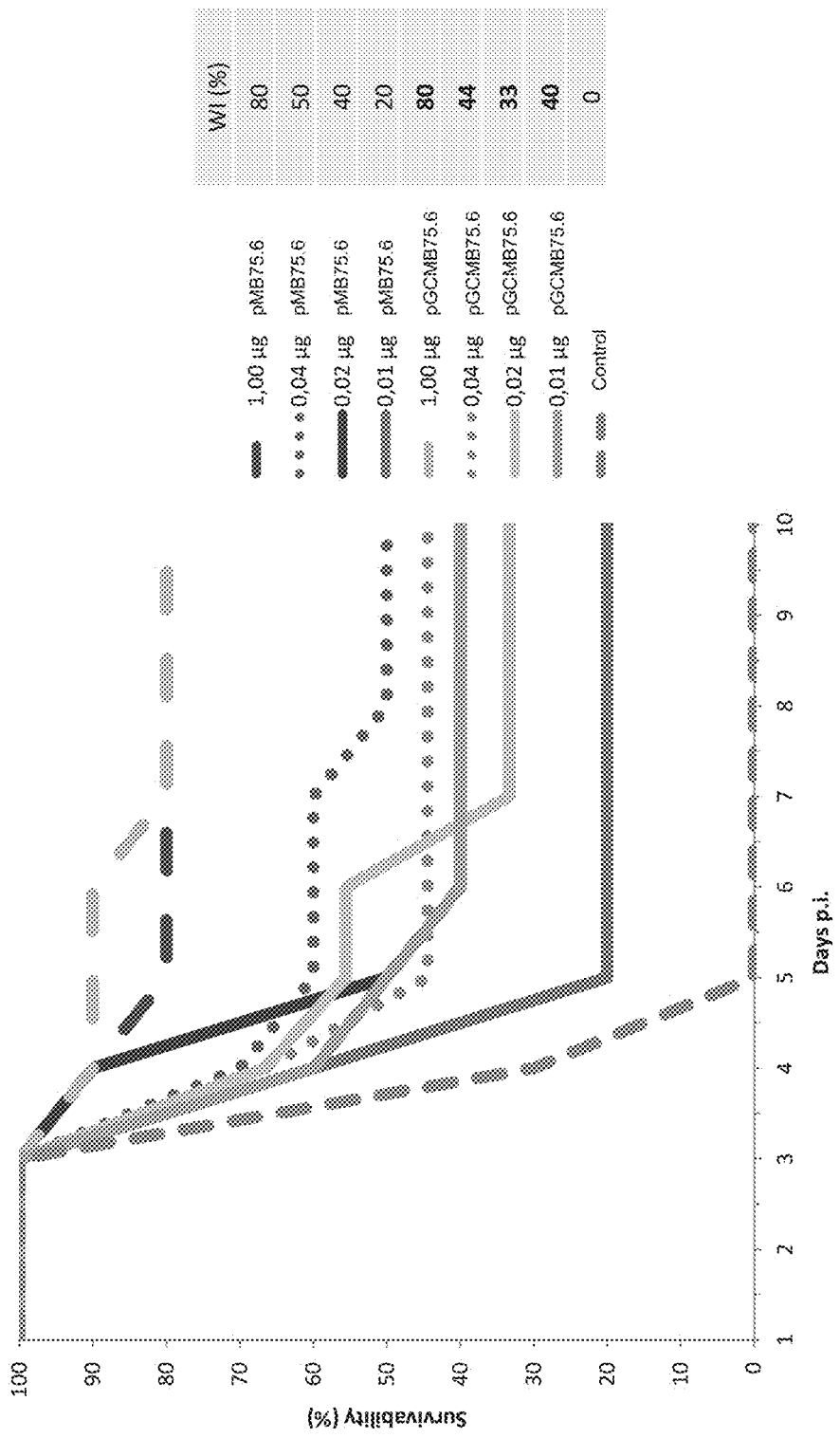

```
                        SEQUENCE LISTING

<160> NUMBER OF SEQ ID NOS: 17

<210> SEQ ID NO 1
<211> LENGTH: 4242
<212> TYPE: DNA
<213> ORGANISM: Artificial sequence
<220> FEATURE:
<223> OTHER INFORMATION: Nucleotide sequence of plasmid pGCMB75.6

<400> SEQUENCE: 1
tgaccgccca acgaccccg cccattgacg tcaataatga cgtatgttcc catagtaacg      60
ccaataggga ctttccattg acgtcaatgg gtggagtatt tacggtaaac tgcccacttg     120
gcagtacatc aagtgtatca tatgccaagt ccgccccta ttgacgtcaa tgacggtaaa     180
tggcccgcct ggcattatgc ccagtacatg accttacggg actttcctac ttggcagtac     240
atctacgtat tagtcatcgc tattaccatg gtgatgcggt tttggcagta catcaatggg     300
cgtggatagc ggtttgactc acggggattt ccaagtctcc accccattga cgtcaatggg     360
agtttgtttt ggcaccaaaa tcaacgggac tttccaaaat gtcgtaacaa ctccgcccca     420
ttgacgcaaa tgggcggtag gcgtgtacgg tgggaggtct atataagcag agctcgttta     480
gtgaaccgtc agatcgcctg gagacgccat ccacgctgtt ttgacctcca tagaagacac     540
cgggaccgat ccagcctccc ctcgaagccg atctgataac ggtaccgata agctggcggc     600
cgattaagct acagaagttg gtcgtgaggc actgggcagg taagtatcaa ggttacaaga     660
```

```
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc cgcaagcttg atatcgaatt cctgcagccc    840
gggggatcca ctagttctag agcggccgcc accgcggtgg agctcgaatt atcagatcga    900
ttaataacta tgctcaaaaa ttgtgtacct ttagctttt aatttgtaaa ggggttaata     960
aggaatattt gatgtatagt gccttgacta gagatcataa tcagccatac cacatttgta   1020
gaggttttac ttgctttaaa aaacctccca cacctccccc tgaacctgaa acataaaatg   1080
aatgcaattg ttgttgttaa cttgtttatt gcagcttata atggttacaa ataaagcaat   1140
agcatcacaa atttcacaaa taaagcattt ttttcactgc attctagttg tggtttgtcc   1200
aaactcatca atgtatctta tcatgtctgg atcatcagat ctgccggtct ccctatagtg   1260
agtcgtatta atttcgataa gccaggttaa cctgcattaa tgaatcggcc aacgcgcggg   1320
gagaggcggt ttgcgtattg ggcgctcttc cgcttcctcg ctcactgact cgctgcgctc   1380
ggtcgttcgg ctgcggcgag cggtatcagc tcactcaaag gcggtaatac ggttatccac   1440
agaatcaggg gataacgcag gaaagaacat gtgagcaaaa ggccagcaaa aggccaggaa   1500
ccgtaaaaag gccgcgttgc tggcgttttt ccataggctc cgcccccctg acgagcatca   1560
caaaaatcga cgctcaagtc agaggtggcg aaacccgaca ggactataaa gataccaggc   1620
gtttccccct ggaagctccc tcgtgcgctc tcctgttccg accctgccgc ttaccggata   1680
cctgtccgcc tttctccctt cgggaagcgt ggcgctttct catagctcac gctgtaggta   1740
tctcagttcg gtgtaggtcg ttcgctccaa gctgggctgt gtgcacgaac cccccgttca   1800
gcccgaccgc tgcgccttat ccggtaacta tcgtcttgag tccaacccgg taagacacga   1860
cttatcgcca ctggcagcag ccactggtaa caggattagc agagcgaggt atgtaggcgg   1920
tgctacagag ttcttgaagt ggtggcctaa ctacggctac actagaagaa cagtatttgg   1980
tatctgcgct ctgctgaagc cagttacctt cggaaaaaga gttggtagct cttgatccgg   2040
caaacaaacc accgctggta gcggtggttt ttttgtttgc aagcagcaga ttacgcgcag   2100
aaaaaaagga tctcaagaag atcctttgat cttttctacg gggtctgacg ctcagtggaa   2160
cgaaaactca cgttaaggga ttttggtcat gggcgcgcct aggcttttgc aaagatcgat   2220
caagagacag gatgaggatc gtttcgcagc ttttcattct gactgcaacg ggcaataagt   2280
ctctgtgtgg attaaaaaaa gagtgtctga tagcagcttc tgaactggtt acctgccgtg   2340
agtaaattaa aattttattg acttaggtca ctaaggcgcc ttgcgctgag gttgcgtcgt   2400
gatatcatca gggcagaccg gttacatccc cctaacaagc tgtataaaga gaaatactat   2460
ctcattggcg ttgcccgcac ctgacagtgc gacgttgggc tgcgtccgtc gaccaacggt   2520
accgaggtaa cagcccaatc tatccatgat ctcggccagg ccgggtcggc cgttatgcag   2580
cccggctcgg gtatgaagcc attaaggagc gacccagcg cgaccgggcg gccggtcacg   2640
ctgcctctgc tgaagcctgc ctgtcactcc ctgcgcggcg tacccgccgt tctcatcgag   2700
taggctccgg atcgcgaccc cggacgggcc ctgggcccag gagcggccta tgacaaatgc   2760
cgggtagcga tccggcattc agcattgact gcgcacggat ccagtccttg caggagcctt   2820
atgccgaccg tagcaaaaaa tgagcccgag ccgatcgcga ttgtgatcc ggtcccgccg    2880 attccggtc gcgatgacgg tcctgtgtaa gcgttatcgt taccaattgt ttaagaagta   2940
tatacgctac gaggtacttg ataacttctg cgtagcatac atgaggtttt gtataaaaat   3000
```

```
ggcgggcgat atcaacgcag tgtcagaaat ccgaaacagt ctgcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taaacaaata ggggttccgc gcacatttcc ccgaaaagtg    3300
ccacctaaat tgtaagcgtt aatattttgt taaaattcgc gttaaatttt tgttaaatca    3360
gctcattttt taaccaatag gccgaaatcg gcaaaatccc ttataaatca aagaataga    3420 ccgagatagg gttgagtgtt gttccagttt ggaacaagag tccactatta agaacgtgg    3480 actccaacgt caaagggcga aaaccgtct atcagggcga tggcccacta cgtgaaccat    3540
caccctaatc aagttttttg gggtcgaggt gccgtaaagc actaaatcgg aaccctaaag    3600 ggagccccg atttagagct tgacggggaa agccggcgaa cgtggcgaga aaggaaggga    3660
agaaagcgaa aggagcgggc gctagggcgc tggcaagtgt agcggtcacg ctgcgcgtaa    3720
ccaccacacc cgccgcgctt aatgcgccgc tacagggcgc gtcccattcg ccattcaggc    3780
tgcgcaactg ttgggaaggg cgatcggtgc gggcctcttc gctattacgc cagctggcga    3840
aagggggatg tgctgcaagg cgattaagtt gggtaacgcc agggttttcc cagtcacgac    3900
gttgtaaaac gacggccagt gagcgcgcgt aatacgactc actataggc gaattgggta    3960 ccgggccccc cctcgagcag gatctataca ttgaatcaat attggcaatt agccatatta    4020
gtcattggtt atatagcata atcaatatt ggctattggc cattgcatac gttgtatcta    4080
tatcataata tgtacattta tattggctca tgtccaatat gaccgccatg ttgacattga    4140
ttattgacta gttattaata gtaatcaatt acggggtcat tagttcatag cccatatatg    4200
gagttccgcg ttacataact tacggtaaat ggcccgcctg gc                       4242
```

<210> SEQ ID NO 2
<211> LENGTH: 4242
<212> TYPE: DNA
<213> ORGANISM: Artificial sequence
<220> FEATURE:
<223> OTHER INFORMATION: Nucleotide sequence of plasmid pMB75.6

<400> SEQUENCE: 2

```
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat gggtaccgg    660 gccccccctc gagcaggatc tatacattga atcaatattg gcaattagcc atattagtca    720
ttggttatat agcataaatc aatattggct attggccatt gcatacgttg tatctatatc    780
ataatatgta catttatatt ggctcatgtc caatatgacc gccatgttga cattgattat    840
```

```
tgactagtta ttaatagtaa tcaattacgg ggtcattagt tcatagccca tatatggagt    900
tccgcgttac ataacttacg gtaaatggcc cgcctggctg accgcccaac gacccccgcc    960
cattgacgtc aataatgacg tatgttccca tagtaacgcc aatagggact ttccattgac   1020
gtcaatgggt ggagtattta cggtaaactg cccacttggc agtacatcaa gtgtatcata   1080
tgccaagtcc gccccctatt gacgtcaatg acggtaaatg gcccgcctgg cattatgccc   1140
agtacatgac cttacgggac tttcctactt ggcagtacat ctacgtatta gtcatcgcta   1200
ttaccatggt gatgcggttt tggcagtaca tcaatgggcg tggatagcgg tttgactcac   1260
ggggatttcc aagtctccac cccattgacg tcaatgggag tttgttttgg caccaaaatc   1320
aacgggactt tccaaaatgt cgtaacaact ccgccccatt gacgcaaatg ggcggtaggc   1380
gtgtacggtg ggaggtctat ataagcagag ctcgtttagt gaaccgtcag atcgcctgga   1440
gacgccatcc acgctgtttt gacctccata aagacaccg ggaccgatcc agcctcccct    1500
cgaagccgat ctgataacgg taccgataag ctggcggccg attaagctac agaagttggt   1560
cgtgaggcac tgggcaggta agtatcaagg ttacaagaca ggtttaagga gaccaataga   1620
aactgggctt gtcgagacag agaagactct tgcgtttctg ataggcacct attggtctta   1680
ctgacatcca ctttgccttt ctctccacag gtgtccactc ccaggttcaa ttacagctct   1740
taagcagccg caagcttgat atcgaattcc tgcagcccgg gggatccact agttctagag   1800
cggccgccac cgcggtggag ctcgaattat cagatcgatt aataactatg ctcaaaaatt   1860
gtgtacctttt agctttttaa tttgtaaagg ggttaataag gaatatttga tgtatagtgc   1920
cttgactaga gatcataatc agccatacca catttgtaga ggttttactt gctttaaaaa   1980
acctcccaca cctcccctg aacctgaaac ataaaatgaa tgcaattgtt gttgttaact    2040
tgtttattgc agcttataat ggttacaaat aaagcaatag catcacaaat ttcacaaata   2100
aagcattttt tcactgcat tctagttgtg gtttgtccaa actcatcaat gtatcttatc    2160
atgtctggat catcagatct gccggtctcc ctatagtgag tcgtattaat ttcgataagc   2220
caggttaacc tgcattaatg aatcggccaa cgcgcgggga gaggcggttt gcgtattggg   2280
cgctcttccg cttcctcgct cactgactcg ctgcgctcgg tcgttcggct gcggcgagcg   2340
gtatcagctc actcaaaggc ggtaatacgg ttatccacag aatcagggga taacgcagga   2400
aagaacatgt gagcaaaagg ccagcaaaag gccaggaacc gtaaaaaggc cgcgttgctg   2460
gcgtttttcc ataggctccg cccccctgac gagcatcaca aaaatcgacg ctcaagtcag   2520
aggtggcgaa acccgacagg actataaaga taccaggcgt ttccccctgg aagctccctc   2580
gtgcgctctc ctgttccgac cctgccgctt accggatacc tgtccgcctt tctcccttcg   2640
ggaagcgtgg cgctttctca tagctcacgc tgtaggtatc tcagttcggt gtaggtcgtt   2700
cgctccaagc tgggctgtgt gcacgaaccc cccgttcagc ccgaccgctg cgccttatcc   2760
ggtaactatc gtcttgagtc aacccggta agacacgact tatcgccact ggcagcagcc    2820
actggtaaca ggattagcag agcgaggtat gtaggcggtg ctacagagtt cttgaagtgg   2880
tggcctaact acggctacac tagaagaaca gtatttggta tctgcgctct gctgaagcca   2940
gttaccttcg gaaaagagt tggtagctct tgatccggca acaaaccac cgctggtagc     3000
ggtggttttt tgtttgcaa gcagcagatt acgcgcagaa aaaaggatc tcaagaagat    3060
cctttgatct tttctacggg gtctgacgct cagtggaacg aaaactcacg ttaagggatt   3120
ttggtcatga gcgcgcctag gcttttgcaa agatcgatca agagacagga tgaggatcgt   3180
```

```
ttcgcatgat tgaacaagat ggattgcacg caggttctcc ggccgcttgg gtggagaggc    3240
tattcggcta tgactgggca caacagacaa tcggctgctc tgatgccgcc gtgttccggc    3300
tgtcagcgca ggggcgcccg gttcttttg tcaagaccga cctgtccggt gccctgaatg    3360
aactgcaaga cgaggcagcg cggctatcgt ggctggccac gacgggcgtt ccttgcgcag    3420
ctgtgctcga cgttgtcact gaagcgggaa gggactggct gctattgggc gaagtgccgg    3480
ggcaggatct cctgtcatct caccttgctc ctgccgagaa agtatccatc atggctgatg    3540
caatgcggcg gctgcatacg cttgatccgg ctacctgccc attcgaccac caagcgaaac    3600
atcgcatcga gcgagcacgt actcggatgg aagccggtct tgtcgatcag gatgatctgg    3660
acgaagagca tcagggctc gcgccagccg aactgttcgc caggctcaag gcgagcatgc    3720
ccgacgcgca ggatctcgtc gtgacccatg gcgatgcctg cttgccgaat atcatggtgg    3780
aaaatggccg cttttctgga ttcatcgact gtggccggct gggtgtggcg gaccgctatc    3840
aggacatagc gttggctacc cgtgatattg ctgaagagct tggcggcgaa tgggctgacc    3900
gcttcctcgt gctttacggt atcgccgctc ccgattcgca gcgcatcgcc ttctatcgcc    3960
ttcttgacga gttcttctga gcgggactct ggggttcgaa atgaccgacc aagcgacgcc    4020
caacctgcca tcacgagatt tcgattccac cgccgccttc tatgaaaggt tgggcttcgg    4080
aatcgttttc cgggacgccg gctggatgat cctccagcgc ggggatctca tgctggagtt    4140
cttcgcccac cctaggcgcg ctcatgagcg gatacatatt tgaatgtatt tagaaaaata    4200
aacaaatagg ggttccgcgc acatttcccc gaaaagtgcc ac                       4242
```

<210> SEQ ID NO 3
<211> LENGTH: 4242
<212> TYPE: DNA
<213> ORGANISM: Artificial sequence
<220> FEATURE:
<223> OTHER INFORMATION: Nucleotide sequence of plasmid pMB75.6_AscI

<400> SEQUENCE: 3

```
tgaccgccca acgaccccg cccattgacg tcaataatga cgtatgttcc catagtaacg     60 ccaatagga ctttccattg acgtcaatgg gtggagtatt tacggtaaac tgcccacttg    120
gcagtacatc aagtgtatca tatgccaagt ccgcccccta ttgacgtcaa tgacggtaaa    180
tggcccgcct ggcattatgc ccagtacatg accttacggg actttcctac ttggcagtac    240
atctacgtat tagtcatcgc tattaccatg gtgatgcggt tttggcagta catcaatggg    300
cgtggatagc ggtttgactc acggggattt ccaagtctcc accccattga cgtcaatggg    360
agtttgtttt ggcaccaaaa tcaacgggac tttccaaaat gtcgtaacaa ctccgcccca    420
ttgacgcaaa tgggcggtag gcgtgtacgg tgggaggtct atataagcag agctcgttta    480
gtgaaccgtc agatcgcctg gagacgccat ccacgctgtt ttgacctcca tagaagacac    540
cgggaccgat ccagcctccc ctcgaagccg atctgataac ggtaccgata agctggcggc    600
cgattaagct acagaagttg gtcgtgaggc actgggcagg taagtatcaa ggttacaaga    660
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc gcaagcttg atatcgaatt cctgcagccc    840
gggggatcca ctagtctag agcggccgcc accgcggtgg agctcgaatt atcagatcga    900
ttaataacta tgctcaaaaa ttgtgtacct ttagcttttt aatttgtaaa ggggttaata    960
aggaatattt gatgtatagt gccttgacta gagatcataa tcagccatac cacatttgta   1020
```

```
gaggttttac ttgctttaaa aaacctccca cacctccccc tgaacctgaa acataaaatg    1080
aatgcaattg ttgttgttaa cttgtttatt gcagcttata atggttacaa ataaagcaat    1140
agcatcacaa atttcacaaa taaagcattt ttttcactgc attctagttg tggtttgtcc    1200
aaactcatca atgtatctta tcatgtctgg atcatcagat ctgccggtct ccctatagtg    1260
agtcgtatta atttcgataa gccaggttaa cctgcattaa tgaatcggcc aacgcgcggg    1320
gagaggcggt ttgcgtattg ggcgctcttc cgcttcctcg ctcactgact cgctgcgctc    1380
ggtcgttcgg ctgcggcgag cggtatcagc tcactcaaag gcggtaatac ggttatccac    1440
agaatcaggg gataacgcag gaaagaacat gtgagcaaaa ggccagcaaa aggccaggaa    1500
ccgtaaaaag gccgcgttgc tggcgttttt ccataggctc cgcccccctg acgagcatca    1560
caaaaatcga cgctcaagtc agaggtggcg aaacccgaca ggactataaa gataccaggc    1620
gtttccccct ggaagctccc tcgtgcgctc tcctgttccg accctgccgc ttaccggata    1680
cctgtccgcc tttctccctt cgggaagcgt ggcgctttct catagctcac gctgtaggta    1740
tctcagttcg gtgtaggtcg ttcgctccaa gctgggctgt gtgcacgaac cccccgttca    1800
gcccgaccgc tgcgccttat ccggtaacta tcgtcttgag tccaacccgg taagacacga    1860
cttatcgcca ctggcagcag ccactggtaa caggattagc agagcgaggt atgtaggcgg    1920
tgctacagag ttcttgaagt ggtggcctaa ctacggctac actagaagaa cagtatttgg    1980
tatctgcgct ctgctgaagc cagttacctt cggaaaaaga gttggtagct cttgatccgg    2040
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
caagagacag gatgaggatc gtttcgcatg attgaacaag atggattgca cgcaggttct    2280
ccggccgctt gggtggagag gctattcggc tatgactggg cacaacagac aatcggctgc    2340
tctgatgccg ccgtgttccg gctgtcagcg caggggcgcc cggttctttt tgtcaagacc    2400
gacctgtccg gtgccctgaa tgaactgcaa gacgaggcag cgcggctatc gtggctggcc    2460
acgacgggcg ttccttgcgc agctgtgctc gacgttgtca ctgaagcggg aagggactgg    2520
ctgctattgg gcgaagtgcc ggggcaggat ctcctgtcat ctcaccttgc tcctgccgag    2580
aaagtatcca tcatggctga tgcaatgcgg cggctgcata cgcttgatcc ggctacctgc    2640
ccattcgacc accaagcgaa acatcgcatc gagcgagcac gtactcggat ggaagccggt    2700
cttgtcgatc aggatgatct ggacgaagag catcaggggc tcgcgccagc cgaactgttc    2760
gccaggctca aggcgagcat gcccgacggc gaggatctcg tcgtgaccca tggcgatgcc    2820
tgcttgccga atatcatggt ggaaaatggc cgcttttctg gattcatcga ctgtggccgg    2880
ctgggtgtgg cggaccgcta tcaggacata gcgttggcta cccgtgatat tgctgaagag    2940
cttggcggcg aatgggctga ccgcttcctc gtgctttacg gtatcgccgc tcccgattcg    3000
cagcgcatcg ccttctatcg ccttcttgac gagttcttct gagcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taacaaata ggggttccgc gcacatttcc ccgaaaagtg    3300
ccacctaaat tgtaagcgtt aatattttgt taaaattcgc gttaaatttt tgttaaatca    3360
```

```
gctcattttt taaccaatag gccgaaatcg gcaaaatccc ttataaatca aaagaataga    3420
ccgagatagg gttgagtgtt gttccagttt ggaacaagag tccactatta agaacgtgg     3480
actccaacgt caaagggcga aaaccgtct atcagggcga tggcccacta cgtgaaccat     3540
caccctaatc aagttttttg gggtcgaggt gccgtaaagc actaaatcgg aaccctaaag    3600
ggagcccccg atttagagct tgacggggaa agccggcgaa cgtggcgaga aggaaggga     3660
agaaagcgaa aggagcgggc gctagggcgc tggcaagtgt agcggtcacg ctgcgcgtaa    3720
ccaccacacc cgccgcgctt aatgcgccgc tacagggcgc gtcccattcg ccattcaggc    3780
tgcgcaactg ttgggaaggg cgatcggtgc gggcctcttc gctattacgc cagctggcga    3840
aagggggatg tgctgcaagg cgattaagtt gggtaacgcc agggttttcc cagtcacgac    3900
gttgtaaaac gacggccagt gagcgcgcgt aatacgactc actataggc gaattgggta     3960
ccgggccccc cctcgagcag gatctataca ttgaatcaat attggcaatt agccatatta    4020
gtcattggtt atatagcata aatcaatatt ggctattggc cattgcatac gttgtatcta    4080
tatcataata tgtacattta tattggctca tgtccaatat gaccgccatg ttgacattga    4140
ttattgacta gttattaata gtaatcaatt acgggtcat tagttcatag cccatatatg     4200
gagttccgcg ttacataact tacggtaaat ggcccgcctg gc                      4242
```

<210> SEQ ID NO 4
<211> LENGTH: 4242
<212> TYPE: DNA
<213> ORGANISM: Artificial sequence
<220> FEATURE:
<223> OTHER INFORMATION: Nucelotide sequence of plasmid pLacZMB75.6

<400> SEQUENCE: 4

```
tgaccgccca acgaccccg cccattgacg tcaataatga cgtatgttcc catagtaacg       60
ccaataggga ctttccattg acgtcaatgg gtggagtatt tacggtaaac tgcccacttg     120
gcagtacatc aagtgtatca tatgccaagt ccgcccccta ttgacgtcaa tgacggtaaa    180
tggcccgcct ggcattatgc ccagtacatg accttacggg actttcctac ttggcagtac    240
atctacgtat tagtcatcgc tattaccatg gtgatgcggt tttggcagta catcaatggg    300
cgtggatagc ggtttgactc acggggattt ccaagtctcc accccattga cgtcaatggg    360
agtttgtttt ggcaccaaaa tcaacgggac tttccaaaat gtcgtaacaa ctccgcccca    420
ttgacgcaaa tgggcggtag gcgtgtacgg tgggaggtct atataagcag agctcgttta    480
gtgaaccgtc agatcgcctg gagacgccat ccacgctgtt ttgacctcca tagaagacac    540
cgggaccgat ccagcctccc ctcgaagccg atctgataac ggtaccgata agctggcggc    600
cgattaagct acagaagttg gtcgtgaggc actgggcagg taagtatcaa ggttacaaga    660
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc cgccaaaaca aaattcctca aaaatcatca    840
tcgaatgaat ggtgaaataa tttccctgaa taactgtagt gttttcaggg cgcggcataa    900
taattaacta tgctcaaaaa ttgtgtacct ttagcttttt aatttgtaaa ggggttaata    960
aggaatattt gatgtatagt gccttgacta gagatcataa tcagccatac cacatttgta   1020
gaggttttac ttgctttaaa aaacctccca cacctccccc tgaacctgaa acataaaatg   1080
aatgcaattg ttgttgttaa cttgtttatt gcagcttata atggttacaa ataaagcaat   1140
agcatcacaa atttcacaaa taaagcattt ttttcactgc attctagttg tggtttgtcc   1200
```

-continued

```
aaactcatca atgtatctta tcatgtctgg atcatcagat ctgccggtct ccctatagtg    1260
agtcgtatta atttcgataa gccaggttaa cctgcattaa tgaatcggcc aacgcgcggg    1320
gagaggcggt ttgcgtattg ggcgctcttc cgcttcctcg ctcactgact cgctgcgctc    1380
ggtcgttcgg ctgcggcgag cggtatcagc tcactcaaag gcggtaatac ggttatccac    1440
agaatcaggg gataacgcag gaaagaacat gtgagcaaaa ggccagcaaa aggccaggaa    1500
ccgtaaaaag gccgcgttgc tggcgttttt ccataggctc cgcccccctg acgagcatca    1560
caaaaatcga cgctcaagtc agaggtggcg aaacccgaca ggactataaa gataccaggc    1620
gtttccccct ggaagctccc tcgtgcgctc tcctgttccg accctgccgc ttaccggata    1680
cctgtccgcc tttctccctt cgggaagcgt ggcgctttct catagctcac gctgtaggta    1740
tctcagttcg gtgtaggtcg ttcgctccaa gctgggctgt gtgcacgaac cccccgttca    1800
gcccgaccgc tgcgccttat ccggtaacta tcgtcttgag tccaacccgg taagacacga    1860
cttatcgcca ctggcagcag ccactggtaa caggattagc agagcgaggt atgtaggcgg    1920
tgctacagag ttcttgaagt ggtggcctaa ctacggctac actagaagaa cagtatttgg    1980
tatctgcgct ctgctgaagc cagttacctt cggaaaaaga gttggtagct cttgatccgg    2040
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
caagagacag gatgaggatc gtttcgcagc ttttcattct gactgcaacg ggcaataagt    2280
ctctgtgtgg attaaaaaaa gagtgtctga tagcagcttc tgaactggtt acctgccgtg    2340
agtaaattaa aattttattg acttaggtca ctaaggcgcc ttgcgctgag gttgcgtcgt    2400
gatatcatca gggcagaccg gttacatccc cctaacaagc tgtataaaga gaaatactat    2460
ctcattggcg ttgcccgcac ctgacagtgc gacgttgggc tgcgtccgtc gaccaacggt    2520
accgaggtaa cagcccaatc tatccatgat ctcggccagg ccgggtcggc cgttatgcag    2580
cccggctcgg gtatgaagcc attaaggagc cgacccagcg cgaccgggcg ccggtcacg    2640 ctgcctctgc tgaagcctgc ctgtcactcc ctgcgcggcg tacccgccgt tctcatcgag    2700
taggctccgg atcgcgaccc cggacggggc ctgggcccag gagcggccta tgacaaatgc    2760
cgggtagcga tccggcattc agcattgact gcgcacggat ccagtccttg caggagcctt    2820
atgccgaccg tagcaaaaaa tgagcccgag ccgatcgcga ttgtgatcc ggtcccgccg    2880 attgccggtc gcgatgacgg tcctgtgtaa gcgttatcgt taccaattgt ttaagaagta    2940
tatacgctac gaggtacttg ataacttctg cgtagcatac atgaggtttt gtataaaaat    3000
ggcgggcgat atcaacgcag tgtcagaaat ccgaaacagt ctgcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taaacaaata ggggttccgc gcacatttcc ccgaaaagtg    3300
ccacctaaat tgtaagcgtt aatattttgt taaaattcgc gttaaatttt tgttaaatca    3360
gctcattttt taaccaatag gccgaaatcg gcaaaatccc ttataaatca aagaatagac    3420
ccgagatagg gttgagtgtt gttccagttt ggaacaagag tccactatta agaacgtgg    3480 actccaacgt caaagggcga aaaccgtct atcagggcga tggcccacta cgtgaaccat    3540
```

-continued

| | |
|---|---|
| caccctaatc aagttttttg gggtcgaggt gccgtaaagc actaaatcgg aaccctaaag | 3600 |
| ggagcccccg atttagagct tgacggggaa agccggcgaa cgtggcgaga aaggaaggga | 3660 |
| agaaagcgaa aggagcgggc gctagggcgc tggcaagtgt agcggtcacg ctgcgcgtaa | 3720 |
| ccaccacacc cgccgcgctt aatgcgccgc tacagggcgc gtcccattcg ccattcaggc | 3780 |
| tgcgcaactg ttgggaaggg cgatcggtgc gggcctcttc gctattacgc cagctggcga | 3840 |
| aaggggatg tgctgcaagg cgattaagtt gggtaacgcc agggttttcc cagtcacgac | 3900 |
| gttgtaaaac gacggccagt gagcgcgcgt aatacgactc actatagggc gaattgggta | 3960 |
| ccgggccccc cctcgaggtc gacggtatcg ataagcttga tatcgaattc ctgcagcccg | 4020 |
| ggggatccac tagttctaga gcggccgcca ccgcggtgga gctccagctt tgttcccctt | 4080 |
| tagtgagggt taattgcgcg cttggcgtaa tcatggtcat agctgtttcc tgtgtgaaat | 4140 |
| tgttatccgc tcacaattcc acacaacata cgagccggaa gcataaagtg taaagcctgg | 4200 |
| ggtgcctaat gagtgagcta actcacatta attgcgttgc gc | 4242 |

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
gtgcgcggaa cccctatttg      20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
gcgtacccgc cgttctcatc      20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
gtctgacgct cagtggaacg      20

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
gttccagttt ggaacaagag tc      22

<210> SEQ ID NO 9
<211> LENGTH: 20
<212> TYPE: DNA
<213> ORGANISM: Artificial sequence
<220> FEATURE:
<223> OTHER INFORMATION: Primer

```
<400> SEQUENCE: 9
ggcaattagc catattagtc                                               20

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
gcagagctcg tttagtgaac cg                                            22

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
gatcataatc agccatacca c                                             21

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
cgtcttgagt ccaacccggt aagacac                                       27

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
ccacaggtgt ccactcccag gttc                                          24

<210> SEQ ID NO 14
<211> LENGTH: 21
<212> TYPE: DNA
<213> ORGANISM: Artificial sequence
<220> FEATURE:
<223> OTHER INFORMATION: Primer

<400> SEQUENCE: 14
ctagtcaagg cactatacat c                                             21

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
tccacagaat cagggggataa cg                                           22

<210> SEQ ID NO 16
```

```
<211> LENGTH: 23
<212> TYPE: DNA
<213> ORGANISM: Artificial sequence
<220> FEATURE:
<223> OTHER INFORMATION: Primer

<400> SEQUENCE: 16
gctcactcat taggcacccc agg                                         23

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
cgcgtaatac gactcactat ag                                          22
```

IMMUNOSTIMULATORY PLASMIDS

REFERENCE TO RELATED APPLICATION

This application claims the benefit of U.S. Provisional Application Ser. No. 61/946,372, filed Feb. 28, 2014, the entire disclosure of which is incorporated herein by reference.

FIELD OF THE INVENTION

The present invention generally relates to immunostimulatory plasmids. The plasmids do not comprise an antibiotic resistance gene. The plasmids can comprise a selectable or screenable marker gene that is not an antibiotic resistance gene (e.g., a LacZ gene). Alternatively, the plasmids can be devoid of any selectable or screenable marker genes.

BACKGROUND OF THE INVENTION

Unmethylated CpG motifs occur much more frequently in bacterial DNA than in vertebrate DNA. These motifs activate host defense mechanisms and lead to innate and acquired immune responses. CpG motifs and their immunostimulatory effects are reviewed in Krieg, Ann. Rev. Immunol. 20:709-760 (2002).

An immunostimulatory plasmid containing a number of CpG motifs was previously developed and has been shown to be effective for eliciting immune responses when administered to avian and bovine species in an immunomodulator composition comprising the plasmid and a cationic liposome delivery vehicle. See U.S. Patent Application Publications Nos. 2012/0064151 A1 (avian species) and 2013/0295167 A1 (bovine species), the contents of both of which are hereby incorporated by reference in their entirety. This plasmid, pMB75.6, is 4242 bp in length and contains 288 CpG dinucleotides. A map of pMB75.6 is shown in FIG. 1 and the nucleotide sequence of pMB75.6 is provided as SEQ ID NO: 2. As described in U.S. Patent Application Publication No. 2012/0064151, the immunomodulator composition containing pMB75.6 elicited a non-antigen-specific immune response that protected chickens from infectious disease when administered in ovo. This non-antigen-specific immune response was further enhanced with administration of at least one biological agent, such as a vaccine. In addition, the immunomodulator composition containing the pMB75.6 plasmid was found to have an adjuvant effect and to elicit an increase in the efficacy of vaccines. Similarly, as described in U.S. Patent Application No. 2013/0295167, the immunomodulator composition containing pMB75.6 elicited a non-antigen-specific immune response in cattle that protected the cattle from infectious disease.

However, as shown in FIG. 1, the pMB75.6 plasmid contains a kanamycin-resistance gene ($Kan^R$). Antibiotic-based selection and production systems are becoming increasingly disfavored due to concerns about horizontal transfer of the antibiotic resistance gene to bacteria in the environment. Potential horizontal transfer of antibiotic resistance genes is particularly concerning for vectors that are directly administered to a subject (e.g., immunostimulatory plasmids such as pMB75.6 or vectors used for gene therapy or DNA vaccination). There is therefore a need in the art for immunostimulatory plasmids that are capable of eliciting an immune response in a subject while also lacking antibiotic resistance genes.

SUMMARY OF THE INVENTION

The present invention relates to immunostimulatory plasmids. The immunostimulatory plasmid may comprise a nucleic acid sequence having at least 89% sequence identity with the sequence of SEQ ID NO: 1, SEQ ID NO: 4, or a combination thereof. In some aspects, the immunostimulatory plasmid may comprise a nucleic acid molecule having at least 84% sequence identity with the sequence of SEQ ID NO: 4. In some aspects, the immunostimulatory plasmid may comprise the sequence of SEQ ID NO: 1. In some aspects, the immunostimulatory plasmid may comprise the sequence of SEQ ID NO: 4.

In other aspects, the immunostimulatory plasmid may consist of a nucleic acid sequence having at least 89% sequence identity with the sequence of SEQ ID NO: 1, SEQ ID NO: 4, or a combination thereof. In some aspects, the immunostimulatory plasmid may consist of a nucleic acid molecule having at least 84% sequence identity with the sequence of SEQ ID NO: 4. In some aspects, the immunostimulatory plasmid may consist of the sequence of SEQ ID NO: 1. In some aspects, the immunostimulatory plasmid may consist of the sequence of SEQ ID NO: 4.

In some aspects, the immunostimulatory plasmid preferably does not comprise a nucleic acid sequence encoding a full-length or functional selectable or screenable marker. In other aspects, the immunostimulatory plasmid comprises a nucleic acid sequence encoding a selectable or screenable marker that is not an antibiotic resistance gene.

The present invention also relates to pharmaceutical formulations comprising any of the immunostimulatory plasmids, or DNA sequences, described herein and a pharmaceutically acceptable carrier.

The present invention further relates to immunomodulator compositions comprising a cationic liposome delivery vehicle and any of the immunostimulatory plasmids, or DNA sequences, described herein.

In some aspects, the present invention relates to methods of using the immunostimulatory plasmids, or DNA sequences, described herein. Suitable methods of use include therapeutic administration to a subject. Such therapeutic administration includes prophylactic treatment, metaphylactic treatment, and post-infection treatment of a subject or subjects.

The present invention relates to methods of stimulating or eliciting an immune response in a subject. In some aspects, the methods include stimulating an immune response in a subject by administering to the subject an immunomodulator composition described herein. In some aspects, the methods include stimulating an immune response in a subject by administering to the subject an immunostimulatory plasmid, or DNA sequence, described herein.

Other objects and features will be in part apparent and in part pointed out hereinafter.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A and FIG. 4B each graphically illustrates that immunomodulator compositions described herein increase the survivability of recipient subjects challenged with a pathogenic virus.

DETAILED DESCRIPTION OF THE INVENTION

Figure 1:
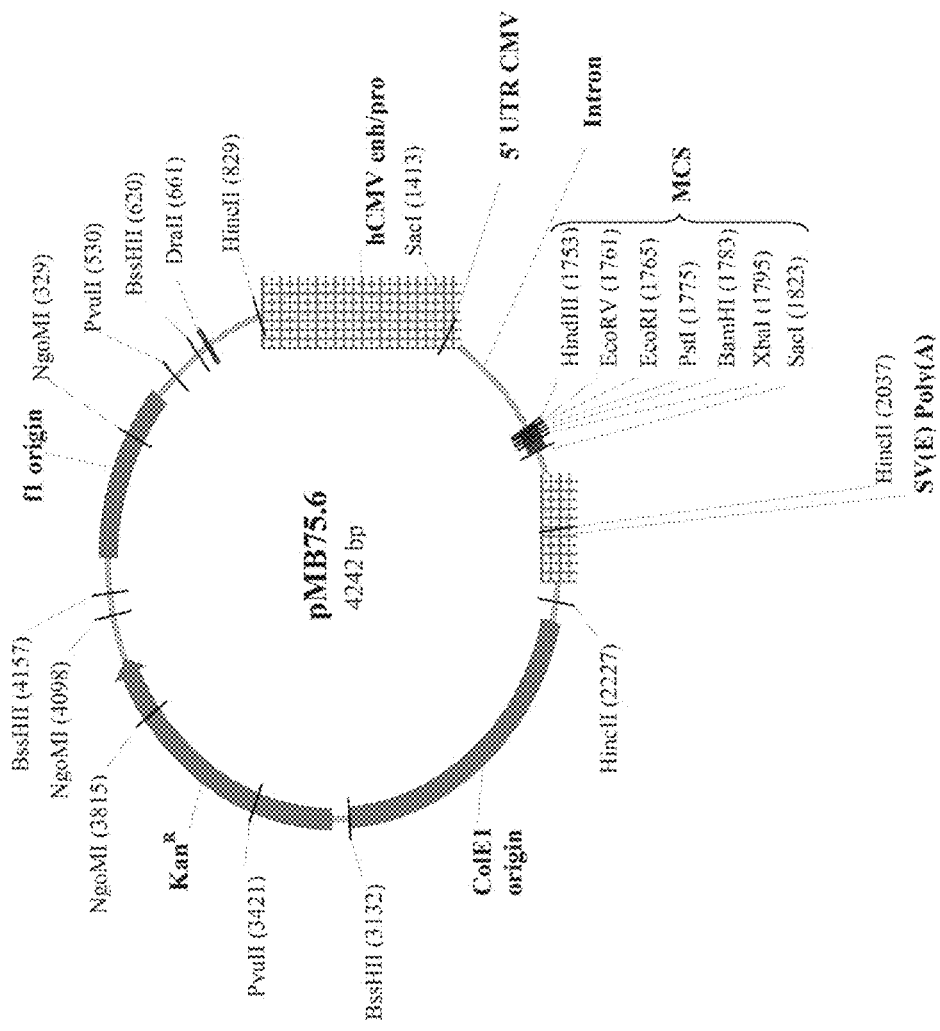
FIG. 1 shows a map of the pMB75.6 plasmid.

In accordance with the present invention, a composition that is capable of eliciting an immune response in a recipient subject, as well as methods of use, have been discovered. In particular, the present invention relates to novel nucleic acid compositions, or immunomodulator compositions, and uses thereof. It has been discovered that such immunomodulator compositions may include DNA sequences described herein with enhanced GC content, CpG motifs, and propagated without including antibiotic resistance genes or coding sequence. The nucleic acid sequences of the invention may be used to stimulate or enhance an immune response in a subject to prevent or treat infectious disease with significantly enhanced safety over other methods of prevention and treatment known in the art. The invention is particularly useful in the treatment and prevention of infectious diseases caused by microorganisms, such as, without limitation, viruses, bacteria, mold, fungus, yeast, parasites and other microbes known in the art. The compositions and methods of using the immunomodulator compositions are discussed in more detail below.

I. Compositions

Compositions useful in this invention, such as those described herein, are generally able to be used as a prophylactic therapy, metaphylactic therapy, or treatment therapy for infectious diseases. Such compositions are referred to herein as immunomodulator compositions. The immunomodulator compositions include at least a immunostimulatory plasmid or immunostimulatory DNA sequence, capable of eliciting an immune response in a recipient subject. In some aspects, the immunomodulator compositions may also include a liposome delivery vehicle.

A. Nucleic Acids

In some aspects the present invention relates to nucleic acid molecules useful for the treatment or prevention of infectious disease causing agents. The nucleic acid molecules described herein may be included in an immunostimulatory plasmid, as linear double stranded or single stranded DNA, amino acid sequence, ribonucleic acid (RNA), or combinations thereof. In some aspects, the present invention relates to nucleic acid molecules, vectors, and host cells (in vitro, in vivo, or ex vivo) which contain the immunostimulatory plasmid or immunostimulatory DNA sequence.

In some aspects, the present invention relates to immunostimulatory plasmids, or DNA sequences, that do not comprise an antibiotic resistance gene. The plasmids may be devoid of any selectable or screenable marker genes. For example, the pGCMB75.6 plasmid described herein does not comprise any full-length or functional selectable or screenable marker genes. The sequence of pGCMB75.6 is provided in SEQ ID NO: 1.

In some aspects, the immunostimulatory plasmids described herein preferably do not comprise a nucleic acid sequence coding for a full-length or functional selectable or screenable marker. In some aspects, the immunostimulatory plasmids do not comprise an antibiotic resistance gene. For example, the plasmids do not comprise a kanamycin resistance gene. In some aspects, the plasmids described herein preferably do not encode an immunogen.

Figure 3:
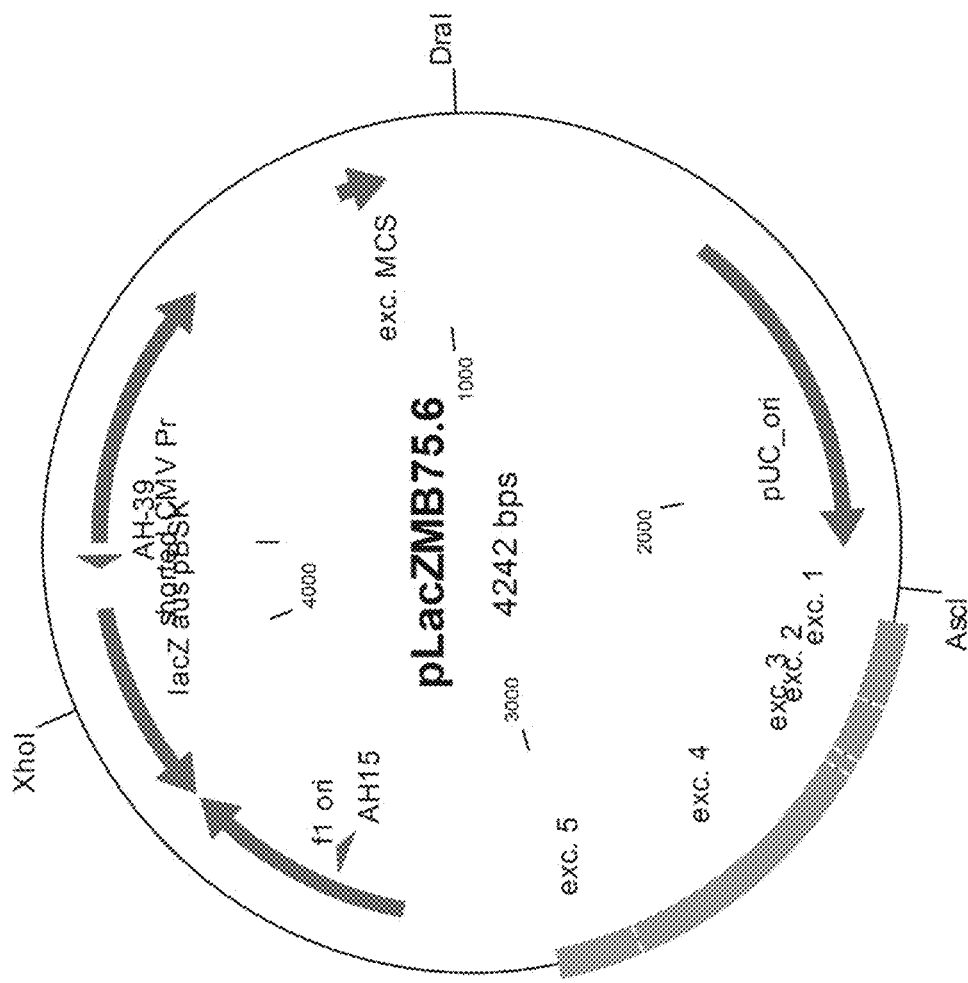
FIG. 3 shows a map of the pLacZ75.6 plasmid.

In some aspects, the immunostimulatory plasmids may comprise a nucleic acid sequence coding for a selectable or screenable marker gene that is not an antibiotic resistance gene. For example, the pLacZMB75.6 plasmid described herein comprises a LacZ gene as a screenable marker. A map of pLacZMB75.6 is provided in FIG. 3 and the nucleotide sequence of pLacZMB75.6 is provided as SEQ ID NO: 4. As shown in FIG. 3, pLacZMB75.6 is similar to pGCMB75.6, but contains a LacZ screenable marker.

It will be appreciated that the nucleotide sequences of the pGCMB75.6 or pLacZMB75.6 plasmids may be varied to a certain extent without significantly adversely affecting their immunostimulatory properties. In some aspects, the present invention relates to an immunostimulatory plasmid comprising a nucleic acid sequence having at least 89% sequence identity with the sequence of pGCMB75.6 (SEQ ID NO: 1). The immunostimulatory plasmid preferably comprises a nucleic acid sequence having at least 90%, at least 91%, at least 92%, at least 93%, at least 94%, at least 95%, at least 96%, at least 97%, at least 98%, or at least 99% sequence identity with the sequence of pGCMB75.6 (SEQ ID NO: 1). In some aspects, the immunostimulatory plasmid more preferably comprises the sequence of pGCMB75.6 (SEQ ID NO: 1).

In some aspects, the present invention relates to an immunostimulatory plasmid comprising a nucleic acid sequence having at least 84% sequence identity with the sequence of pLacZMB75.6 (SEQ ID NO: 4). The immunostimulatory plasmid preferably comprises a nucleic acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pLacZMB75.6 (SEQ ID NO: 4). In some aspects, the immunostimulatory plasmid more preferably comprises the sequence of pLacZMB75.6 (SEQ ID NO: 4).

In some aspects, the present invention relates to an immunostimulatory plasmid consisting of a nucleic acid sequence having at least 89% sequence identity with the sequence of pGCMB75.6 (SEQ ID NO: 1). The immunostimulatory plasmid preferably consists of a nucleic acid sequence having at least 90%, at least 91%, at least 92%, at least 93%, at least 94%, at least 95%, at least 96%, at least 97%, at least 98%, or at least 99% sequence identity with the sequence of pGCMB75.6 (SEQ ID NO: 1). In some aspects, the immunostimulatory plasmid more preferably consists of the sequence of pGCMB75.6 (SEQ ID NO: 1).

In some aspects, the present invention relates to an immunostimulatory plasmid consisting of a nucleic acid sequence having at least 84% sequence identity with the sequence of pLacZMB75.6 (SEQ ID NO: 4). The immunostimulatory plasmid preferably consists of a nucleic acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pLacZMB75.6 (SEQ ID NO: 4). In some aspects, the immunostimulatory plasmid more preferably consists of the sequence of pLacZMB75.6 (SEQ ID NO: 4).

Another important aspect of this invention provides for immunostimulatory DNA sequences or immunostimulatory plasmids capable of stimulating an immune response including nucleic acid sequences that hybridize under high stringency conditions to SEQ ID NO: 1 or SEQ ID NO: 4. Suitable nucleic acid sequences include those that are homologous, substantially similar, or identical to the nucleic acids of the present invention. In some aspects, homologous nucleic acid sequences will have a sequence similarity of at least about 89%, 90%, 91%, 92%, 93%, 94%, 95%, 96%, 97%, 98%, 99%, or 100% to SEQ ID NO: 1 or the respective complementary sequence. In other aspects, homologous nucleic acid sequences will have a sequence similarity of at least about 84%, 85%, 86%, 88%, 89%, 90%, 91%, 92%, 93%, 94%, 95%, 96%, 97%, 98%, 99%, or 100% to SEQ ID NO: 4 or the respective complementary sequence. Sequence similarity may be calculated using a number of algorithms known in the art, such as BLAST, described in Altschul, S. F., et al., J. Mol. Biol. 215:403-10, 1990. The nucleic acids may differ in sequence from the above-described nucleic acids due to the degeneracy of the genetic code. In general, a reference sequence will be 18 nucleotides, more usually 30 or more nucleotides, and may comprise the entire nucleic acid sequence of the composition for comparison purposes.

Nucleotide sequences that can hybridize to SEQ ID NO: 1 or SEQ ID NO: 4 are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the invention (Current Protocols in Molecular Biology, Unit 6, pub. John Wiley & Sons, N.Y. 1989).

Mutant nucleotides of the DNA molecules described herein may be used, so long as mutants include nucleic acid sequences maintain the ability to stimulating an immune response as described herein. The DNA sequence of such a mutation will usually differ by one or more nucleotides or amino acids. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. In summary, the invention relates to nucleic acid sequences capable of stimulating an immune response in a subject and variants or mutants thereof. Also, the invention encompasses the intermediatary RNAs encoded by the described nucleic acid sequences, as well as any resultant amino acid sequences encoded.

Where the nucleotide sequence of the immunostimulatory plasmid varies from the sequences provided in SEQ ID NOs. 1 and 4 the CpG dinucleotides in the plasmid are preferably left intact. Alternatively, if the nucleotide sequence of the plasmid is altered such that a CpG dinucleotide is eliminated, the sequence of the plasmid may be altered at another location such that the total number of CpG dinucleotides in the plasmid remains the same. Further CpG dinucleotides in addition to those already present in the nucleotide sequences of pGCMB75.6 or pLacZMB75.6 may also be introduced into the plasmid. Thus, for example, the immunostimulatory plasmids described herein preferably comprise at least about 200, at least about 220, at least about 240, at least about 260, at least about 270, at least about 275, at least about 280, at least about 283, at least about 285, or at least about 288 CpG dinucleotides. For example, the immunostimulatory plasmid can comprise 283 CpG dinucleotides.

In particular, the present invention relates to pharmaceutical formulations comprising any of the immunostimulatory plasmids or DNA sequences described herein and a pharmaceutically acceptable carrier.

B. Immunomodulator

Suitable immunomodulator compositions for use with the immunostimulatory plasmids described herein are described in U.S. Patent Application Publications Nos. 2012/0064151 A1 (avian species) and 2013/0295167 A1 (bovine species), the contents of both of which are hereby incorporated by reference in their entirety.

The immunomodulator composition comprises a liposome delivery vehicle and at least one of the immunostimulatory plasmids, or DNA sequences, described herein.

A suitable liposome delivery vehicle comprises a lipid composition that is capable of delivering nucleic acid molecules to the tissues of the treated subject. A liposome delivery vehicle is preferably capable of remaining stable in a subject for a sufficient amount of time to deliver a nucleic acid molecule and/or a biological agent. For example, the liposome delivery vehicle is stable in the recipient subject for at least about five minutes, for at least about 1 hour, or for at least about 24 hours.

A liposome delivery vehicle of the present invention comprises a lipid composition that is capable of fusing with the plasma membrane of a cell to deliver a nucleic acid molecule into a cell. When the nucleic acid molecule encodes one or more proteins, the nucleic acid:liposome complex preferably has a transfection efficiency of at least about 1 picogram (pg) of protein expressed per milligram (mg) of total tissue protein per microgram (µg) of nucleic acid delivered. For example, the transfection efficiency of a nucleic acid: liposome complex can be at least about 10 pg of protein expressed per mg of total tissue protein per µg of nucleic acid delivered; or at least about 50 pg of protein expressed per mg of total tissue protein per µg of nucleic acid delivered. The transfection efficiency of the complex may be as low as 1 femtogram (fg) of protein expressed per mg of total tissue protein per µg of nucleic acid delivered, with the above amounts being more preferred.

A preferred liposome delivery vehicle of the present invention is between about 100 and 500 nanometers (nm) in diameter. For example, the liposome delivery vehicle can be between about 150 and 450 nm or between about 200 and 400 nm in diameter.

Suitable liposomes include any liposome, such as those commonly used in, for example, gene delivery methods known to those of skill in the art. Preferred liposome delivery vehicles comprise multilamellar vesicle (MLV) lipids and extruded lipids. Methods for preparation of MLVs are well known in the art. More preferred liposome delivery vehicles comprise liposomes having a polycationic lipid composition (i.e., cationic liposomes) and/or liposomes having a cholesterol backbone conjugated to polyethylene glycol. Exemplary cationic liposome compositions include, but are not limited to, N-[1-(2,3-dioleyloxy)propyl]-N,N,N-trimethylammonium chloride (DOTMA) and cholesterol, N-[1-(2,3-dioleoyloxy)propyl]-N,N,N-trimethylammonium chloride (DOTAP) and cholesterol, 1-[2-(oleoyloxy)ethyl]-2-oleyl-3-(2-hydroxyethyl)-imidazolinium chloride (DOTIM) and cholesterol, dimethyldioctadecylammonium bromide (DDAB) and cholesterol, and combinations thereof. A most preferred liposome composition for use as a delivery vehicle includes DOTIM and cholesterol.

A suitable nucleic acid molecule includes any of the immunostimulatory plasmids described herein. Coding nucleic acid sequences encode at least a portion of a protein or peptide, while non-coding sequence does not encode any portion of a protein or peptide. According to the present invention, "non-coding" nucleic acids can include regulatory regions of a transcription unit, such as a promoter region. The term, "empty vector" can be used interchangeably with the term "non-coding," and particularly refers to a nucleic acid sequence in the absence of a protein coding portion, such as a plasmid vector without a gene insert. Expression of a protein encoded by the plasmids described herein is not required for elicitation of a non-antigen-specific immune response; therefore the plasmids need not contain any coding sequences operatively linked to a transcription control sequence. However, further advantages may be obtained (i.e., antigen-specific and enhanced immunity) by including in the composition nucleic acid sequence (DNA or RNA) which encodes an immunogen and/or a cytokine. Such a nucleic acid sequence encoding an immunogen and/or a cytokine can be included in the immunostimulatory plasmids described herein, or can be included in a separate nucleic acid (e.g., a separate plasmid) in the composition.

Complexing a liposome with the immunostimulatory plasmids described herein may be achieved using methods standard in the art or as described in U.S. Pat. No. 6,693,086, the contents of which are hereby incorporated by reference in their entirety. A suitable concentration of a plasmid to add to a liposome includes a concentration effective for delivering a sufficient amount of the plasmid into a subject such that a systemic immune response is elicited. For example, from about 0.1 µg to about 10 µg of plasmid can be combined with about 8 nmol liposomes, from about 0.5 µg to about 5 µg of plasmid can be combined with about 8 nmol liposomes, or about 1.0 µg of plasmid can be combined with about 8 nmol liposomes. The ratio of plasmid to lipid (µg plasmid:nmol lipid) in a composition can be at least about 1:1 plasmid:lipid by weight (e.g., 1 µg plasmid:1 nmol lipid). For example, the ratio of plasmid to lipids can be at least about 1:5, at least about 1:10, or at least about 1:20. Ratios expressed herein are based on the amount of cationic lipid in the composition, and not on the total amount of lipid in the composition. The ratio of plasmid to lipids in a composition of the invention is suitably from about 1:1 to about 1:80 plasmid:lipid by weight; from about 1:2 to about 1:40 plasmid:lipid by weight; from about 1:3 to about 1:30 plasmid:lipid by weight; or from about 1:6 to about 1:15 plasmid:lipid by weight.

C. Biological Agent

Any of the immunomodulator compositions described herein can further comprise at least one biological agent, in addition to the liposome delivery vehicle and at least one of the plasmids described herein.

Suitable biological agents are agents that are effective in preventing or treating avian or bovine diseases. Such biological agents include immune enhancer proteins, immunogens, vaccines, antimicrobials or any combination thereof. Suitable immune enhancer proteins are those proteins known to enhance immunity. By way of a non-limiting example, a cytokine, which includes a family of proteins, is a known immunity enhancing protein family. Suitable immunogens are proteins which elicit a humoral and/or cellular immune response such that administration of the immunogen to a subject mounts an immunogen-specific immune response against the same or similar proteins that are encountered within the tissues of the subject. An immunogen may include a pathogenic antigen expressed by a bacterium, a virus, a parasite or a fungus. Preferred antigens include antigens derived from organisms which cause an infectious disease in a subject. According to the present invention, an immunogen may be any portion of a protein, naturally occurring or synthetically derived, which elicits a humoral and/or cellular immune response. As such, the size of an antigen or immunogen may be as small as about 5-12 amino acids and as large as a full length protein, including any sizes in between. The antigen may be a multimer protein or fusion protein. The antigen may be a purified antigen. Alternatively, the immune enhancer protein or immunogen can be encoded by the immunostimulatory plasmid or by another nucleic acid included in the immunomodulator composition. Where the immune enhancer protein or immunogen is encoded by a nucleic acid molecule in the immunomodulator composition, the nucleic acid sequence encoding the immune enhancer protein or immunogen is operatively linked to a transcription control sequence, such that the immunogen is expressed in a tissue of a subject, thereby eliciting an immunogen-specific immune response in the subject, in addition to the non-specific immune response. Techniques to screen for immunogenicity, such as pathogen antigen immunogenicity or cytokine activity are known to those of skill in the art and include a variety of in vitro and in vivo assays.

Where the biological agent is a vaccine, the vaccine may include a live, infectious, viral, bacterial, or parasite vaccine or a killed, inactivated, viral, bacterial, or parasite vaccine. One or more vaccines, live or killed viral vaccines, may be used in combination with the immunomodulator composition of the present invention. Suitable vaccines include those known in the art for avian or bovine species.

Exemplary vaccines for avian species include, without limitation, those used in the art for protection against Marek's disease virus (MDV), New Castle disease virus (NDV), chick anemia virus (CAV), infectious bursal disease virus (IBDV), infectious bronchitis virus (IBV), turkey herpesvirus (HVT), infectious laryngotracheitis virus (ILTV), avian encephalomyelitis virus (AEV), fowlpox virus (FPV), fowl cholera, avian influenza virus (AIV), reovirus, avian leucosis virus (ALV), reticuloendotheliosis virus (REV), avian adenovirus and hemorrhagic enteritis virus (HEV), coccidia, and other diseases known in the art. In another example, the vaccine may be a vaccine as described by U.S. Pat. Nos. 5,427,791, 6,048,535, and 6,406,702. For example, a vaccine for protection against Marek's disease may be used in combination with the immunomodulator composition of the present invention.

Exemplary vaccine for bovine species include, without limitation, those used in the art for protection against infectious bovine rhinotracheitis (IBR) (Type 1 bovine herpes virus (BHV1)), parainfluenza virus type 3 (PI3), bovine respiratory syncytial virus (BRSV), bovine viral diarrhea virus (BVDV Type 1 and 2), *Histophilus somni, Mycoplasma bovis*, and other diseases known in the art. For example, a vaccine for the protection against *Mannheimia haemolytica* may be used in combination with the immunomodulator composition of the present invention.

The biological agent can be an antimicrobial. Suitable antimicrobials include: quinolones, preferably fluoroquinolones, β-lactams, and macrolide-lincosamide-streptogramin (MLS) antibiotics.

Suitable quinolones include benofloxacin, binfloxacin, cinoxacin, ciprofloxacin, clinafloxacin, danofloxacin, difloxacin, enoxacin, enrofloxacin, fleroxacin, gemifloxacin, ibafloxacin, levofloxacin, lomefloxacin, marbofloxacin, moxifloxacin, norfloxacin, ofloxacin, orbifloxacin, pazufloxacin, pradofloxacin, perfloxacin, sarafloxacin, sparfloxacin, temafloxacin, and tosufloxacin. Preferred fluoroquinolones include ciprofloxacin, danofloxacin, enrofloxacin, moxifloxacin, and pradofloxacin. Suitable naphthyridones include nalidixic acid.

Suitable β-lactams include penicillins (e.g., amoxicillin, ampicillin, azlocillin, benzathine penicillin, benzylpenicillin, carbenicillin, cloxacillin, co-amoxiclav [i.e. amoxicillin/clavulanic acid], dicloxacillin, flucloxacillin, methicillin, mezlocillin, nafcillin, oxacillin, phenoxymethylpenicillin, piperacillin, procaine penicillin, temocillin, and ticarcillin); cephalosporins (e.g., cefaclor, cefalonium, cefamandole, cefapririn, cefazolin, cefepime, cefixime, cefotaxime, cefoxitin, cefpirome, cefpodoxime, cefquinome, ceftazidime, ceftiofur, ceftriaxone, cefuroxime, cephalexin, cephalothin, and defotetan); carbapenems and penems (e.g., doripenem, ertapenem, faropenem, imipenem, and meropenem); monobactams (e.g., aztreonam, nocardicin A, tabtoxinine-β-lactam, and tigemonam); and β-lactamase inhibitors (e.g., clavulanic acid, sulbactam, and tazobactam). Preferred β-lactams include cephalosporins, in particular, cefazolin.

Suitable MLS antibiotics include clindamycin, lincomycin, pirlimycin, and any macrolide antibiotic. A preferred lincosamide antibiotic is pirlimycin.

Other antimicrobials include aminoglycosides, clopidol, dimetridazoles, erythromycin, framycetin, furazolidone, halofuginone, 2-pyridones, robenidine, sulfonamides, tetracyclines, trimethoprim, various pleuromutilins (e.g., tiamulin and valnemulin), and various streptomycin (e.g., monensin, narasin, and salinomycin).

II. Methods

An object of the present invention is to provide immunomodulator compositions, immunostimulatory plasmids (or DNA sequence), and methods that elicit protective immunity to uninfected subjects, protective immunity to infected subjects, enhanced immunity to uninfected subjects, enhanced immunity to infected subjects, therapeutic immunity to infected subjects, or combinations thereof. As such, the compositions of the invention may be used to prophylactically immunize a subject or be used to treat a subject. The methods described herein include administrating an immunostimulatory plasmid, or DNA sequence, described herein to a subject.

A. Methods of Immune Stimulation

The present invention is related to methods of eliciting an immune response in a recipient subject. The methods comprise administering to a subject an effective amount of an immunomodulator composition to elicit an immune response. In some aspects, the immunomodulator composition elicits a non-antigen-specific immune response that is effective alone. In some aspects, the immunomodulator composition enhances the operation of at least one biological agent such as a vaccine, when administered prior to such a vaccine, co-administered with a vaccine, administered post vaccination, or mixed with the vaccine. In some aspects, the methods provide new treatment strategies for protecting recipient subjects from infectious diseases and treating populations having infectious disease. In some aspects, the methods provide a more rapid, a longer and better protection against a disease when the immunomodulator is used in combination with a vaccine, compared to use of the vaccine without the immunomodulator composition.

An immune response can be elicited in a recipient subject by administering an effective amount of an immunomodulator composition, which includes any of the liposome delivery vehicles described herein, any of the immunostimulatory plasmids (for DNA sequences) described herein, and any of the biological agents described herein. It is contemplated that the biological agent may be mixed with or co-administered with the immunomodulator or independently thereof. Independent administration may be prior to or after administration of the immunomodulator. It is also contemplated that more than one administration of the immunomodulator or biological agent may be used to extend enhanced immunity. Furthermore, more than one biological agent may be co-administered with the immunomodulator, administered prior to the immunomodulator, administered after administration of the immunomodulator, or concurrently with the immunomodulator.

An effective amount of any of the immunomodulator compositions described herein may be administered to a subject. The effective amount is sufficient to elicit an immune response in the recipient subject. Such effective amount is any amount that causes an immune response in a recipient subject. Methods of measuring an immune response are well known in the art. Also, a skilled artisan will recognize that the effective amount will depend upon age weight, stage of infection, as well as other factors known in the art. Suitable effective amounts may range from about 0.1 µg to 1,000 µg per subject. In some aspects, the effective amount may range from about 0.1 µg to about 10 µg, from about 0.1 µg to about 5 µg, from about 0.5 µg to about 5 µg, from about 0.25 µg to about 5 µg, from about 0.05 µg to about 10 µg, from about 5 µg to about 15 µg, from about 10 µg to about 15 µg, from about 10 µg to about 20 µg, from about 20 µg to about 30 µg, from about 30 µg to about 40 µg, from about 40 µg to about 50 µg, from about 50 µg to about 70 µg, from about 70 µg to about 90 µg, from about 50 µg to about 100 µg, from about 100 µg to about 150 µg, from about 150 µg to about 200 µg, from about 200 µg to about 250 µg, from about 250 µg to about 300 µg, from about 300 µg to about 350 µg, from about 350 µg to about 400 µg, from about 400 µg to about 450 µg, from about 450 µg, to about 500 µg, from about 500 µg to about 550 µg, from about 550 µg to about 600 µg, from about 600 µg to about 650 µg, from about 650 µg to about 700 µg, from about 700 µg to about 750 µg, from about 750 µg to about 800 µg, from about 800 µg to about 850 µg, from about 850 µg to about 900 µg, from about 900 µg to about 950 µg, from about 950 µg to about 1000 µg. Preferably, in some aspects, the effective amount ranges from about 0.5 µg to about 10 µg. Yet, preferably in other aspects the effective amount ranges from about 50 µg to about 100 µg. And, preferably in other aspects, the effective amount ranges from about 40 µg to about 70 µg.

In some aspects, an immune response can be elicited in a member of the avian species by administering an effective amount of any of the immunomodulator compositions described herein to the member of the avian species. The effective amount is sufficient to elicit an immune response in the member of the avian species. For example, the effective amount of the immunomodulator for an avian species may be from about 0.05 µg to about 10 µg, from about 0.1 µg to about 5 µg, from about 0.5 µg to about 1.5 µg, or from about 1.0 µg to about 10 µg. By way of example, suitable effective amounts for a subject that is of the avian species may be about 0.1 µg, 0.2 µg, 0.3 µg, 0.4 µg, 0.5 µg, 0.6 µg, 0.7 µg, 0.8 µg, 0.9 µg, 1.0 µg, 1.2 µg, 1.4 µg, 1.6 µg, 1.8 µg, 2.0 µg, 2.5 µg, 3.0 µg, 3.5 µg, 4.0 µg, 4.5 µg, 5.0 µg, 5.5 µg, 6.0 µg, 6.5 µg, 7.0 µg, 7.5 µg, 8.0 µg, 8.5 µg, 9.0 µg, 9.5 µg, 10.0 µg, 9.5 µg, 10.0 µg, 10.5 µg, 11.0 µg, 12 µg, 13 µg, 14 µg, or 15 µg.

In some aspects, an immune response can be elicited in a member of the bovine species by administering an effective amount of any of the immunomodulator compositions described herein to the member of the bovine species. The effective amount is sufficient to elicit an immune response in the member of the bovine species. For example, the effective amount of the immunomodulator for a bovine species can be from about 1 µg to about 1000 µg per animal, from about 5 µg to about 500 µg per animal, from about 10 µg to about 100 µg per animal, from about 10 µg to about 50 µg per animal, or from about 40 µg to about 60 µg per animal. By way of example, suitable effective amounts for a subject that is of the bovine species may be about 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg, 200 µg or up to 500 µg, or up to 1000 µg.

B. Conditions for Use

The methods of the invention elicit an immune response in a subject such that the subject is protected from a disease that is amenable to elicitation of an immune response. As used herein, the phrase "protected from a disease" refers to reducing the symptoms of the disease; reducing the occurrence of the disease; reducing the clinical or pathologic severity of the disease; or reducing shedding of a pathogen causing a disease. Protecting a subject can refer to the ability of a therapeutic composition of the present invention, when administered to a subject, to prevent a disease from occurring, cure, and/or alleviate or reduce disease symptoms, clinical signs, pathology, or causes. For example, without limitation, clinical signs of Bovine Respiratory Disease (BRD) include lung lesions, increased temperature, depression (e.g. anorexia, reduced responsiveness to external stimuli, droopy ears), nasal discharge, and respiratory character (e.g. respiratory rate, respiratory effort). The immunomodulator compositions described herein may be administered to cattle that are suspected of being exposed to BRD to prevent or reduce the severity of the above-described clinical signs of BRD. By way of further example, without limitation, clinical signs of Marek's disease in avian subjects includes reduced hatchability and bird survivability. The immunomodulator compositions described herein may be administered to avian subjects that are suspected of being exposed to Marek's disease virus to prevent or reduce the severity of the above-described clinical signs of Marek's disease.

As such, protecting a subject from a disease encompasses both preventing disease occurrence (prophylactic treatment) and treating a subject that has a disease (therapeutic treatment). In particular, protecting a subject from a disease is accomplished by eliciting an immune response in the subject by inducing a beneficial or protective immune response which may, in some instances, additionally suppress, reduce, inhibit, or block an overactive or harmful immune response. The term "disease" refers to any deviation from the normal health of a subject and includes a state when disease symptoms are present, as well as conditions in which a deviation (e.g., infection, gene mutation, genetic defect, etc.) has occurred, but symptoms are not yet manifested.

Methods of the invention may be used for the prevention of disease, stimulation of effector cell immunity against disease, elimination of disease, alleviation of disease, and prevention of a secondary disease resulting from the occurrence of a primary disease.

In some aspects, methods described herein may be used to improve the acquired immune response of the subject when co-administered with a vaccine versus administration of the vaccine by itself. Generally a vaccine once administered does not immediately protect the subject as it takes time to stimulate acquired immunity. The term "improve" refers, in the present invention, to elicitation of an innate immune response in the subject until the vaccine starts to protect the subject and/or to prolong the period of protection, via acquired immunity, given by the vaccine.

In some aspects, methods of the invention include administering the composition to protect against infection of a wide variety of pathogens. The composition administered may or may not include a specific antigen to elicit a specific response. It is contemplated that the methods of the invention will protect the recipient subject from disease resulting from infectious microbial agents including, without limitation, viruses, bacteria, fungi, and parasites. A skilled artisan will recognize and appreciate that a immunomodulator composition, as described herein, is effective against numerous infectious agents, which are too numerous to list. The infectious agents provided herein are provided for exemplary purposes and are provided without limitation of the scope of use.

Exemplary viral infectious diseases in avian species include, without limitation, those resulting from infection with chicken infectious anemia virus (CIAV), Marek's disease virus (MDV), herpesvirus chicken (HCV), herpesvirus turkey (HTV), infectious bursal disease virus (IBDV), Newcastle disease virus (NDV), infectious bronchitis virus (IBV), infectious laryngotracheitis virus (ILTV), paramyxovirus type 3, avian encephalomyelitis (AEV), fowlpox virus (FPV), fowl cholera, avian influenza virus (AIV), reovirus, avian leucosis virus (ALV), reticuloendotheliosis virus (REV), avian adenovirus, hemorrhagic enteritis virus (HEV), pneumovirus, pigeon pox virus, recombinants thereof, and other viruses known in the art.

Exemplary bacterial infections in avian species include, without limitation, those resulting from infection with gram positive bacteria, gram negative bacteria, or fungi such as *Bordetella* spp., *Campylobacter jejuni, Clostridium botulinum, Clostridium colinum, Clostridium perfringens, Erysipelothrix insidiosa, Escherichia coli, Hemophilus gallinarum, Mycoplasma gallisepticum, Mycoplasma meleagridis, Mycoplasma synoviae, Pasteurella multocida, Riemerella anatipestifer, Salmonella* spp., *Salmonella enteritidis, Salmonella gallinarum, Salmonella pullorum*, and other bacteria known in the art.

Exemplary fungi or mold infections in avian species include, without limitation, those resulting from infection with *Aspergillus flavus, Aspergillus fumigates, Candida albicans*, and other infectious fungi or mold known in the art. Exemplary disease conditions include, without limitation, those resulting from toxins from gram positive bacteria, gram negative bacteria, or fungi such as *Clostridium botulinum* toxin, *Clostridium perfringens* toxins, *Escherichia coli* enterotoxin, Fusarium mycotoxins *Pasteurella* leukotoxin, *Staphylococcus* toxins, and other toxins known in the art.

Exemplary parasites in avian species include, without limitation, *Ascaridia galli, Capillaria annulata, Capillaria contorta, Capillaria obsignata, coccidia* spp., *Eimeria meleagridis, Heterakis gallinae, Syngamus trachea*, and other parasites known in the art.

Exemplary viral infectious diseases in bovine species include, without limitation, those resulting from infection with bluetongue virus, bovine adenovirus, bovine calicivirus, bovine coronavirus (BCV), bovine enterovirus, bovine herpesvirus Type 1 (BHV1), bovine herpesvirus Type 4 (BHV4), bovine leukemia virus, bovine parvovirus, bovine reovirus, bovine respiratory syncytial virus (BRSV), bovine rhinovirus, bovine viral diarrhea virus Type 1 (BVDV1), bovine viral diarrhea virus Type 2 (BVDV2), infectious bovine rhinotracheitis (IBR), malignant catarrhal fever virus, parainfluenza virus type 3 (PIV3), rabies virus, vesicular stomatitis virus (VSV), recombinants thereof, and other viruses known in the art.

Exemplary bacterial infections in bovine species include, without limitation, those resulting from infection with gram positive bacteria, gram negative bacteria, or mycobacteria such as *Arcanobacterium pyogenes, Bacillus anthracis, Bacillus anthrax, Brucella abortus, Campylobacter fetus, Campylobacter jejuni, Clostridium botulinum, Clostridium chauveoi, Clostridium colinum, Clostridium hemolyticum, Clostridium novyi, Clostridium perfringens, Clostridium septicum, Clostridium tetani, Corynebacterium, Escherichia coli, Fusobacterium necrophorum, Fusobacterium* spp., *Histophilus somni, Histophilus* spp., *Leptospira* spp., *Mannheimia haemolytica, Moraxella* spp., *Muellerius* spp., *Mycobacterium paratuberculosis, Mycobacterium* spp., *Mycoplasma bovirhinis, Mycoplasma bovis, Mycoplasma dispar, Mycoplasma* spp., *Pasteurella multocida, Salmonella* spp., *Treponema* spp., *Ureaplasma diversum*, and other bacteria known in the art.

Exemplary fungi or mold infections in bovine species includes, without limitation, those resulting from infection with *Actinobacterim* spp., *Aspergillus* spp., and *Histomonas* spp., and other infectious fungi or mold known in the art.

Exemplary parasites in bovine species include, without limitation, *Anaplasma* spp., *Anaplasma marginale, Babesia* spp., *Chorioptes* spp., *Cooperia, Cysticercus* spp., *Damalinia bovis, Dermatophilus* spp., *Dictylocaulus* spp., *Eimeria* spp., *Eperythrozoon* spp., *Fascioloides* spp., *Haemonchus* spp., *Melophagus* spp., *Muellerius* spp., *Nematodirus* spp., *Neospora* spp., *Oestrus* spp., *Ostertagia* spp., *Psoroptes* spp., *Sarcoptes* spp., *Serpens* spp., *Strongyloides* spp., *Toxoplasma* spp., *Trichophyton* spp., *Trichostrongylus, Trichuris* spp., and *Tritrichomonas* spp., and other parasites known in the art.

Exemplary infectious disease agents in bovine species also include those agents causing mastitis, metritis, cryptosporidiosis, and any other infectious disease the bovine species is susceptible to.

C. Administration

A variety of administration routes are available. The particular mode selected will depend, of course, upon the particular biological agents selected, the age and general health status of the subject, the particular condition being treated and the dosage required for therapeutic efficacy. The methods of this invention may be practiced using any mode of administration that produces effective levels of an immune response without causing clinically unacceptable adverse effects. The compositions may conveniently be presented in unit dosage form and may be prepared by any of the methods well known in the art.

The immunomodulator composition may be administered intravenously, intramuscularly, intradermally, intraperitoneally, subcutaneously, by spray, in ovo by feather follicle method, orally, intraocularly, intratracheally, intranasally, or by other methods known in the art. In one aspect, the immunomodulator is administered subcutaneously. In another aspect, the immunomodulator may be administered intramuscularly. In another aspect, the immunomodulator is administered as a spray. In another aspect, the immunomodulator may be administered orally.

In one respect, the immunomodulator may be administered by itself to the subject prior to challenge (or infection). In another aspect, the immunomodulator may be administered by itself to the subject post challenge (or infection). In another aspect, the immunomodulator may be administered by itself to the subject at the same time as challenge (or infection).

In some aspects, the immunomodulator composition may be co-administered at the same time as the vaccination prior to challenge. In some aspects, the immunomodulator composition may be co-administered at the same time as the vaccination at the same time as challenge (or infection). In some aspects, the co-administration may include administering the vaccine and immunomodulator in the same general location on the subject at two different sites next to each other (i.e., injections next to each other at the neck of the subject), on opposing sides of the subject at the same general location (i.e., one on each side of the neck), or on different locations of the same subject. In some aspects, the immunomodulator composition can be administered prior to vaccination and challenge. In some aspects, the immunomodulator composition may be administered after vaccination but prior to challenge. The immunomodulator composition can be administered after challenge to a subject that has been vaccinated prior to challenge (or infection).

A skilled artisan will recognize that administration routes may vary depending upon the subject and the health or state of the subject. The administration routes provided for avian and bovine species are for exemplary purposes and are provided without limitation.

Vaccination of avian species may be performed at any age. Vaccinations may be administered to 18 day old embryos (in ovo) and above for a live microorganism and 3 weeks and older for an inactivated microorganism or other type of vaccine. For in ovo vaccination, vaccination may be administered in the last quarter of development. The vaccine may be administered subcutaneously, by the feather follicle method, by spray, orally, intraocularly, intratracheally, intranasally, in ovo, or by other methods know in the art. Oral vaccines may be administered in drinking water. Further, it is contemplated that the methods of the invention may be used based on routine vaccination schedules.

The immunomodulator composition may also be administered to an avian species subcutaneously, by the feather follicle method, by spray, intraocularly, intratracheally, intranasally, in ovo, or by other methods known in the art. For example, the immunomodulator composition can be administered in ovo. Alternatively, the immunomodulator composition can be administered as a spray.

The immunomodulator composition can be administered in ovo to an avian embryo in the last quarter of its development. For example, the immunomodulator composition can be administered in ovo to a 18-day-old or 19-day-old embryo. The administration to the egg may be prior to challenge (or infection) or post challenge.

The immunomodulator can be administered to an animal of the avian or bovine species from about 1 to about 14 days prior to challenge or from about 1 to about 14 days post challenge. For example, the immunomodulator can be administered from about 1 to about 7 days prior to challenge or from about 1 to about 7 days post challenge. The immunomodulator is suitably administered 1, 2, 3, 4, 5, 6, 7 days prior to challenge or 1, 2, 3, 4, 5, 6, 7 days post challenge.

Vaccination of bovine species may be performed at any age. The vaccine may be administered intravenously, intramuscularly, intradermally, intraperitoneally, subcutaneously, by spray, orally, intraocularly, intratracheally, intranasally, or by other methods known in the art. Further, it is contemplated that the methods described herein may be used based on routine vaccination schedules.

Other delivery systems may include time-release, delayed release, or sustained release delivery systems. Such systems can avoid repeated administrations of the compositions therefore increasing convenience. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109.

Delivery systems also include non-polymer systems that are lipids including sterols such as cholesterol, cholesterol esters, and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to, erosional systems in which an agent of the invention is contained in a form within a matrix such as those described in U.S. Pat. Nos. 4,452,775, 4,675,189, and 5,736,152, and diffusional systems in which an active component permeates at a controlled rate from a polymer such as described in U.S. Pat. Nos. 3,854,480, 5,133,974, and 5,407,686. In addition, pump-based hardware delivery systems can be used, some of which are adapted for implantation.

As various changes could be made in the above composition, products, and methods without departing from the scope of the invention, it is intended that all matter contained in the above description and in the examples given below shall be interpreted as illustrative and not in a limiting sense.

Definitions

The term "effective amount" refers to the amount necessary or sufficient to realize a desired biologic effect. For example, an effective amount of immunomodulator for treating or preventing an infectious disease is that amount necessary to cause the development of an immune response upon exposure to the microbe, thus causing a reduction in the amount of microbe within the subject and preferably the eradication of the microbe. The effective amount for any particular application can vary depending on such factors as the disease or condition being treated, the size of the subject, or the severity of the disease or condition. One of ordinary skill in the art can empirically determine the effective amount of immunomodulator without necessitating undue experimentation.

The term "cytokine" refers to an immune enhancing protein family. The cytokine family includes hematopoietic growth factor, interleukins, interferons, immunoglobulin superfamily molecules, tumor necrosis factor family molecules and chemokines (i.e. proteins that regulate the migration and activation of cells, particularly phagocytic cells). Exemplary cytokines include, without limitation, interleukin-2 (IL-2), interleukin-12 (IL-12), interleukin-15 (IL-15), interleukin-18 (IL-18), interferon-$\alpha$ (IFN$\alpha$), and interferon-$\gamma$ (IFN$\gamma$).

The term "elicit" can be used interchangeably with the terms activate, stimulate, generate or upregulate.

The term "eliciting an immune response" in a subject refers to specifically controlling or influencing the activity of the immune response, and can include activating an immune response, upregulating an immune response, enhancing an immune response and/or altering an immune response (such as by eliciting a type of immune response which in turn changes the prevalent type of immune response in a subject from one which is harmful or ineffective to one which is beneficial or protective).

The term "operatively linked" refers to linking a nucleic acid molecule to a transcription control sequence in a manner such that the molecule is able to be expressed when transfected (i.e., transformed, transduced or transfected) into a host cell. Transcriptional control sequences are sequences which control the initiation, elongation, and termination of transcription. Particularly important transcription control sequences are those which control transcription initiation, such as promoter, enhancer, operator and repressor sequences. A variety of such transcription control sequences are known to those skilled in the art. Preferred transcription control sequences include those which function in avian, fish, mammalian, bacteria, viral, plant, and insect cells. While any transcriptional control sequences may be used with the invention, the sequences may include naturally occurring transcription control sequences naturally associated with a sequence encoding an immunogen or immune stimulating protein.

The terms "nucleic acid molecule" and "nucleic acid sequence" can be used interchangeably and include DNA, RNA, or derivatives of either DNA or RNA. The terms also include oligonucleotides and larger sequences such as plasmids, such as the immunostimulatory plasmids described herein, and including both nucleic acid molecules that encode a protein or a fragment thereof, and nucleic acid molecules that comprise regulatory regions, introns, or other non-coding DNA or RNA. Typically, an oligonucleotide has a nucleic acid sequence from about 1 to about 500 nucleotides, and more typically, is at least about 5 nucleotides in length. The nucleic acid molecule can be derived from any source, including mammalian, fish, bacterial, insect, viral, plant, synthetic sources or combinations thereof. A nucleic acid molecule can be produced by methods commonly known in the art such as recombinant DNA technology (e.g., polymerase chain reaction (PCR), amplification, cloning) or chemical synthesis. Nucleic acid molecules include natural nucleic acid molecules and homologues thereof, including, but not limited to, natural allelic variants and modified nucleic acid molecules in which nucleotides have been inserted, deleted, substituted, or inverted in such a manner that such modifications do not substantially interfere with the nucleic acid molecule's ability to elicit an immune response useful in the methods of the present invention. A nucleic acid homologue may be produced using a number of methods known to those skilled in the art (see, for example, Sambrook et al., *Molecular Cloning: A Laboratory Manual*, Cold Spring Harbor Labs Press, 1989), which is incorporated herein by reference.

The terms "selectable marker" and "selectable marker gene" refer to a gene that encodes a product that protects the organism in which the gene is expressed from a selective agent (e.g., an antibiotic) or a condition that would normally kill the organism or inhibit its growth. Selectable marker genes are most commonly antibiotic resistance genes (e.g., kanamycin resistance genes, ampicillin resistance genes, chloramphenicol resistance genes, tetracycline resistance genes, etc.). Thus, for example, when *E. coli* cells are subjected to a transformation procedure to introduce a plasmid encoding a kanamycin resistance gene and then grown on or in media containing kanamycin, only the *E. coli* cells that have successfully taken up the plasmid and expressed the kanamycin resistance gene will survive. The terms "selectable marker" and "selectable marker gene" also include genes that code for enzymes involved in the synthesis of a compound that is essential for the growth of an organism. When introduced into an auxotrophic organism that is unable to synthesize the essential compound, such genes allow the organism to grow in a medium that has been supplemented with the essential compound. For example, bacterial cells that are auxotrophic for the amino acid lysine due to a mutation in or the absence of an enzyme involved in lysine biosynthesis normally are unable to grown on media that has not been supplemented with lysine. When such bacteria are subjected to a transformation procedure to introduce a plasmid encoding the enzyme involved in lysine biosynthesis, the bacteria that have successfully taken up the plasmid and expressed the enzyme will survive when grown on media that has not been supplemented with lysine. The terms "selectable marker" and "selectable marker gene" further include genes that allow for poison/antidote selection. For example, the ccdB gene encodes a protein that binds to DNA gyrase, an essential enzyme for cell division. Upon binding to DNA gyrase, the ccdB gene product impairs gene replication and induces cell death. Thus, bacterial expressing the ccdB gene product cannot survive. The ccdA gene encodes a protein (the "antidote") that acts as a natural inhibitor of the ccdB gene product. Thus, when bacteria having the ccdB gene in their bacterial genome are subjected to a transformation procedure to introduce a plasmid encoding the ccdA gene product, only the cells that successfully take up the plasmid and express the ccdA gene will survive.

The terms "screenable marker" and "screenable marker gene" refer to a gene that encodes a product that allows an observer to distinguish between cells expressing the screenable marker gene and cells that are not expressing the screenable marker gene. Screenable marker gene systems are well known in the art and include, for example, lacZ genes and genes encoding fluorescent proteins such as green fluorescent protein (GFP), yellow fluorescent protein (YFP), red fluorescent protein (RFP), blue fluorescent protein (BFP), or cyan fluorescent protein (CFP).

As used herein, the term "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., avian species, bovine species, dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. Subjects may be any member of the avian species, whether domestic or wild, and may be commercially reared for breeding, meat or egg production. Exemplary avian species include, without limitation, chickens, turkeys, geese, ducks, pheasants, quail, pigeons, ostriches, caged birds, birds in zoological collections and aviaries and the like. Subjects may be any member of the bovine species, whether domestic or wild, and may be commercially reared for breeding, meat or mil production. Exemplary bovine species include, without limitation, antelopes, buffalos, yaks, cattle, bison, and the like. Species of cattle include, without limitation, cows, bulls, steers, heifer, ox, beef cattle, dairy cattle, and the like. Subjects may be any member of an aquaculture species, including without limitation, any species of fish, crustaceans, molluscs, living in freshwater or saltwater. In some aspects, subjects may be diagnosed with an infectious disease, may be at risk for an infectious disease, or may be experiencing an infectious disease. Subjects may be of any age including in utero, new born, adolescence, adult, middle age, or elderly.

EXAMPLES

The following non-limiting examples are provided to further illustrate the present invention.

Example 1: Preparation of the pGCMB75.6 Plasmid

Figure 2:
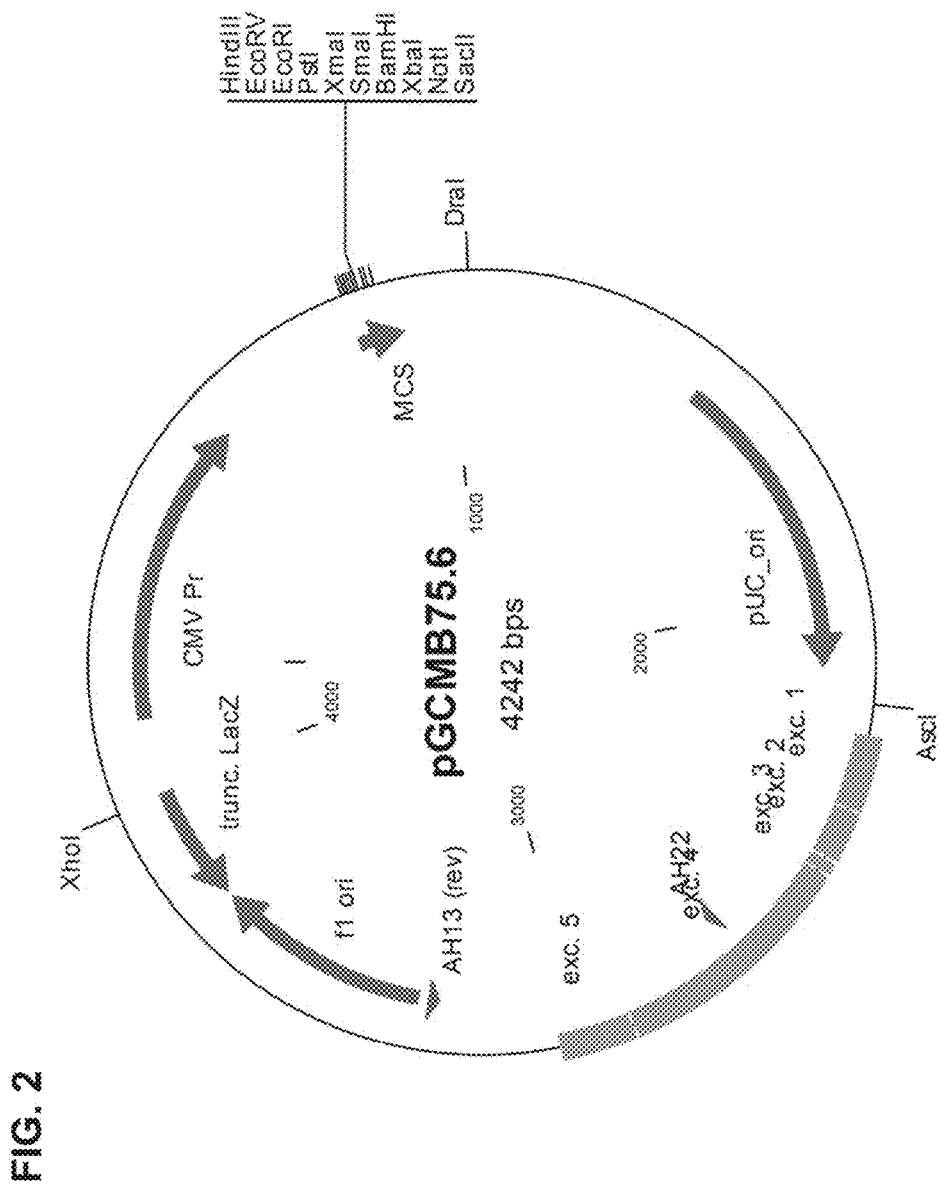
FIG. 2 shows a map of the pGCMB75.6 plasmid.

A map of pGCMB75.6 is shown in FIG. 2. In pGCMB75.6, the kanamycin-resistance gene of pMB75.6 (see FIG. 1) has been replaced by non-coding sequence from E. coli K-12. To generate the pGCMB75.6 plasmid, an AscI single cutter restriction site was introduced into pMB75.6 at a site 5' of the kanamycin resistance gene to generate pMB75.6_AscI (SEQ ID NO: 3). To introduce the AscI restriction site, an adenine present in the sequence of pGCMB75.6 was mutated to a guanine, thereby changing the sequence AGCGCGCC in the pGCMB75.6 plasmid to GGCGCGCC. This modification was accomplished using a mutagenesis-based approach by ligation during amplification. A single primer was used, which carried the AscI restriction site in its middle.

A 1779 nt long AscI (GGCGCGCC)/XhoI (CTCGAG) fragment was synthesized by Life Technologies GmbH (Darmstadt, Germany). This fragment contained five regions comprising non-coding sequence from E. coli K-12 (exchanges 1-5, abbreviated as "exc. 1," "exc. 2," etc. in FIG. 2), an F1 origin of replication, and a truncated lacZ gene (see FIG. 2). In the case of exchange 4, the E. coli sequence was manually changed at several positions in order to increase the GC-content of the plasmid. In addition, in exchange 2, a single nucleotide was changed to delete a DraI restriction site, so that there would only be a single DraI site in the plasmid.

As shown in FIG. 2, pGCMB75.6 contains several regulatory elements (an F1 origin of replication, a CMV promoter, and a pUC origin of replication) and a multiple cloning site. pGCMB75.6 also contains a truncated lacZ gene. However, pGCMB75.6 does not comprise any full-length or functional selectable or screenable marker genes. pGCMB75.6 is 4242 bp in length and contains 283 CpG dinucleotides.

One positive clone, carrying the new introduced AscI site (pMB75.6_AscI) was digested with AscI (GGCGCGCC)/

XhoI (CTCGAG) to generate a 2463 fragment containing the CMV promoter, multiple cloning site, and pUC origin of replication (see FIG. 2). The 1779 nt AscI (GGCGCGCC)/ XhoI (CTCGAG) synthesized fragment was digested with AscI/XhoI as well.

Both fragments (the 2463 nt vector fragment and the 1779 nt insert fragment) were gel eluted from a 1% agarose gel by using the QIAquick Gel Extraction Kit from Qiagen. A ligation was performed using 600 ng of the 1779 nt fragment and 400 ng of the 2463 nt pMB75.6_AscI vector fragment in a total volume of 20 µl, overnight at 16° C. The 20 µl was then dialyzed for 2 h against 20 ml $H_2O$ on ice, and then mixed with 5 µl electro-competent DH5α E. coli cells and 40 µl $H_2O$ (Invitrogen F-f80lacZΔM15 Δ (lacZYA-argF) U169 recA1 endA1 hsdR17 (rk−, mk+) gal-phoA supE44λ-thi-1 gyrA96 relA1; Lot no. 1376481, Part no. 44-0097). Following transformation and 1 h regeneration in SOC media, the cells were plated on LB plates without kanamycin at a $10^{-4}$ dilution. This dilution allowed for isolation of individual clones.

Colony PCR was performed on individual clones using the following primers listed in Table 1.

TABLE 1

| PCR primers. | |
|---|---|
| AH-13 rev | GTGCGCGGAACCCCTATTTG (SEQ ID NO: 5) |
| AH-22 for | GCGTACCCGCCGTTCTCATC (SEQ ID NO: 6) |

The locations of the AH-13 rev and AH-22 for primers are shown in FIG. 2. A premix containing Taq polymerase was used. PCR reactions were loaded onto a 1% agarose gel containing ethidium bromide. Positive clones which carried the correct plasmid (pGCMB75.6) showed a product of 606 bp.

A total of more than 10,000 clones were screened to identify three positive clones. The three positive clones were immediately transferred to fresh LB plates and were used to create 3 Research Cell Banks (RCB; Sys 3733, Sys 3734 and Sys 3735).

In parallel, medium was inoculated with these three clones and plasmid DNA was generated. Complete sequence certification of each of the three subclones was done using the following primers listed in Table 2.

TABLE 2

| PCR for sequence certification. | |
|---|---|
| AH-12 for | GTCTGACGCTCAGTGGAACG (SEQ ID NO: 7) |
| AH-13 rev | GTGCGCGGAACCCCTATTTG (SEQ ID NO: 5) |
| AH-15 | GTTCCAGTTTGGAACAAGAGTC (SEQ ID NO: 8) |
| AH-16 | GGCAATTAGCCATATTAGTC (SEQ ID NO: 9) |
| AH-17 | GCAGAGCTCGTTTAGTGAACCG (SEQ ID NO: 10) |
| AH-18 | GATCATAATCAGCCATACCAC (SEQ ID NO: 11) |
| AH-19 | CGTCTTGAGTCCAACCCGGTAAGACAC (SEQ ID NO: 12) |
| AH-20 | CCACAGGTGTCCACTCCCAGGTTC (SEQ ID NO: 13) |
| AH-21 rev | CTAGTCAAGGCACTATACATC (SEQ ID NO: 14) |
| AH-22 for | GCGTACCCGCCGTTCTCATC (SEQ ID NO: 6) |
| AH-23 | TCCACAGAATCAGGGGATAACG (SEQ ID NO: 15) |

Example 2: Generation of the pLacZMB75.6 Plasmid

To generate the pLacZMB75.6 plasmid (FIG. 3; SEQ ID NO: 4), a 1307 nt XhoI (CTCGAG)/DraI (TTTAAA) fragment was synthesized by Life Technologies GmbH (Darmstadt, Germany) This 1307 nt fragment contained a portion of the lacZ gene (265 nt). Thus, when ligated into pGCMB75.6, this fragment elongates the truncated LacZ gene located upstream of the XhoI restriction site and allows the LacZ gene to be expressed (compare FIG. 2 and FIG. 3). In addition 91 nt of the multiple cloning site were exchanged with E. coli non coding sequence, in order to eliminate sequence homology with the newly introduced LacZ gene region and avoid recombination. In addition, the 5' region of the CMV promoter was deleted (265 nt) in order to generate a plasmid of the same size as plasmid pGCMB75.6.

pGCMB75.6 and the 1311 nt synthesized fragment were both digested with XhoI and DraI. Both fragments were gel eluted from a 1% agarose gel by using the QIAquick Gel Extraction Kit from Qiagen.

A ligation was performed using 240 ng of the 1311 nt fragment and 240 ng of the vector fragment in a total volume of 20 µl, overnight at 16° C. 3 µl were mixed with 10 µl electro-competent DH5α E. coli cells (Invitrogen F-f80lacZΔM15 Δ (lacZYA-argF) U169 recA1 endA1 hsdR17 (rk−, mk+) gal-phoA supE44λ-thi-1 gyrA96 relA1; Lot no. 1376481, Part no. 44-0097) and 40 µl 10% Glycerin solution. Following transformation and 1 h regeneration in SOC media, the cells were plated on LB X-Gal/IPTG plates without kanamycin at a $10^{-2}$ and $10^{-4}$ dilution. This dilution allowed for isolation of individual clones.

Identification of colonies with plasmid was performed via blue/white selection and colony PCR was performed to confirm using the following primers listed in Table 3.

TABLE 3

| PCR primers for colony confirmation. | |
|---|---|
| AH-15 | GTTCCAGTTTGGAACAAGAGTC (SEQ ID NO: 8) |
| AH-39 | GCTCACTCATTAGGCACCCCAGG (SEQ ID NO: 16) |

The locations of the AH-15 and AH-39 primers are shown in FIG. 3. A premix containing Taq polymerase was used. PCR reactions were loaded onto a 1% agarose gel containing ethidium bromide. Positive clones which carried the correct plasmid (pLacZMB75.6) showed a product of 777 bp.

Four positive clones were identified and immediately transferred to fresh LB plates and were used to create Research Cell Banks (RCB; Sys 3736, Sys 3737, Sys 3738 and Sys 3739).

In parallel, medium was inoculated with these four clones and plasmid DNA was generated. Complete sequence certification of each of the four subclones was done using the same primers as for pGCMB75.6 but instead of using primer AH-16 (SEQ ID NO: 10) primer AH-24 was used (See Table 4).

TABLE 4

PCR primer for AH-24.

| | |
|---|---|
| AH-24 | CGCGTAATACGACTCACTATAG (SEQ ID NO. 17) |

Example 3: Immunomodulator Composition

The immunomodulator is a composition comprising a cationic lipid and non-coding DNA sequence described herein. The synthetic immunomodulator lipid components [1-[2-[9-(Z)-octadecenoyloxy]]-2-[8](Z)-heptadecenyl]-3-[hydroxyethyl]imidazolinium chloride (DOTIM) and a synthetic neutral lipid cholesterol are formulated to produce liposomes approximately 200 nm in diameter (See, U.S. Pat. No. 6,693,086). The DNA component is pGCMB75.6 or pLacZMB75.6. Being negatively charged, the plasmid DNA associates with the positively-charged (cationic) liposomes (See, U.S. Pat. No. 6,693,086).

Example 4: Immunomodulator Composition Administration to Mammal Model Increased Survivability in Virus Challenge The efficacy of the immunomodulator compositions described herein was evaluated in a mammal model challenged with pathogen. Mice were administered the immunomodulator composition, containing pGCMB75.6 DNA and cationic liposomes, via intraperitoneal injection. The immunomodulator composition was administered at 0.01 µg, 0.02 µg, 0.04 µg, and 1.00 µg concentrations. Control mice were administered 0.9% NaCl solution via intraperitoneal injection. Twenty-four hours post-immunomodulator administration, all animals were challenged with viral application via intraperitoneal injection (0.2 ml $10^{3.4}$ $KID_{50}$/ml). The challenge virus was Pseudorabies (PR). The survivability rates are depicted in FIG. 4. Mice receiving an immunomodulator composition described herein had higher dose dependent survivability rates than control mice.

Example 5: Immunomodulator Composition Administration to Avian Model Increased Hatchability and Survivability in Pathogen Challenge The efficacy of the immunomodulator compositions described herein was evaluated in an avian model challenged with pathogen by spray on day E19 (embryonic day 19). Chicken eggs were administered an immunomodulator composition, containing pGCMB75.6 DNA and cationic liposomes, via in ovo administration on day E18 (embryonic day 18). Control eggs received a placebo control diluent (D5W) (in ovo). BHI broth (spray) was used as mock challenge (T1). The details of the study treatment groups are provided in Table 5 below.

TABLE 5

Avian Immunomodulator composition treatment descriptions.

| Treatment Group | Number of eggs on study at E18[1] | In ovo administration (Day E18) | Challenge description spray (Day E19) | Number of Flats[2] | Number of Hatching Trays/ sub-trays[3] | Number of pens[4] |
|---|---|---|---|---|---|---|
| T1 | 896 | Placebo Control Diluent (D5W) | BHI broth (mock) | 56 | 7/14 | 14 |
| T2 | 896 | Placebo Control Diluent (D5W) | APEC[5] | 56 | 7/14 | 14 |
| T3 | 896 | 1.0 mcg JV-77/egg | APEC[5] | 56 | 7/14 | 14 |
| T4 | 896 | 0.1 mcg JV-77/egg | APEC[5] | 56 | 7/14 | 14 |
| T5 | 896 | 1.0 mcg Lot X5872/egg | APEC[5] | 56 | 7/14 | 14 |
| T6 | 896 | 0.1 mcg Lot X5972/egg | APEC[5] | 56 | 7/14 | 14 |
| T7 | 896 | 1.0 mcg Lot X5928/egg | APEC[5] | 56 | 7/14 | 14 |
| T8 | 896 | 0.1 mcg Lot X5928/egg | APEC[5] | 56 | 7/14 | 14 |

[1]Day 18 of egg incubation;
[2]16 eggs per flat;
[3]64 eggs per sub-tray (partitioned to accommodate two groups per tray);
[4]The chicks hatched from each section of the tray were transferred to one pen;
[5]Avian pathogenic *Escherichia coli* (APEC).

The DNA component of the immunomodulator composition included one of three clones isolated of pGCMB75.6 DNA (i.e. Jv77, X5872, or X5928). As can be observed from the results summarized in Table 6 below, both the average hatchability and average survivability were improved when an immunomodulator composition described herein was administered compared to eggs receiving control treatment.

TABLE 6

Avian hatchability and survivability rates.*

| Treatment Group | N | Mortality at Hatch (avg.) | Mortality at Hatch (Diff. from Control-Chall.) | Mortality Post-hatch (avg.) | Mortality Post-hatch (Diff. from Control-Chall.) | Overall Mortality (avg.) | Overall Mortality (Diff. from Control-Chall.) |
|---|---|---|---|---|---|---|---|
| 01-Control no challenge | 14 | 12.5% | | 0.7% | | 13.2% | |
| 02-Control Challenge (Chall) | 14 | 22.5% | | 27.8% | | 43.5% | |
| 03-Jv77: 1.0 µg Chall | 14 | 20.2% | −2.3% | 26.5% | −1.3% | 40.6% | −2.9% |
| 04-Jv77: 0.1 µg Chall | 14 | 20.8% | −1.7% | 22.4% | −5.4% | 38.6% (p = 0.0368) | −4.9% |
| 05-X5872: 1.0 µg Chall | 14 | 17.6% (p = 0.0110) | −4.9% | 22.1% | −5.7% | 36.3% (p = 0.0023) | −7.2% |
| 06-X5872: 0.1 µg Chall | 14 | 23.0% | 0.5% | 24.6% | −3.2% | 42.0% | −1.5% |
| 07-X5928: 1.0 µg Chall | 14 | 15.5% (p = 0.0003) | −7.0% | 22.3% | −5.5% | 33.9% (p < 0.0001) | −9.6% |
| 08-X5928: 0.1 µg Chall | 14 | 21.2% | −1.3% | 27.7% | −0.1% | 43.0% | −0.5% |

*All validation tests passed (comparison between two control groups). Significant difference compared with the Control Chall group.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products, compositions, and methods without departing from the scope of the invention, it is intended that all matter contained in the above description and shown in the accompanying drawings shall be interpreted as illustrative and not in a limiting sense.

What is claimed is:

1. An immunostimulatory nucleic acid molecule comprising at least 89% sequence homology with the sequence of SEQ ID NO: 1 and at least 200 CpG dinucleotides, wherein the immunostimulatory nucleic acid molecule is devoid of any full-length screenable or selectable marker, and wherein the immunostimulatory nucleic acid molecule does not code for an immunogen.

2. The immunostimulatory nucleic acid molecule of claim 1, wherein the nucleic acid molecule has at least 91% sequence homology with the sequence of SEQ ID NO: 1.

3. The immunostimulatory nucleic acid molecule of claim 1, wherein the nucleic acid molecule comprises SEQ ID NO: 1.

4. An immunostimulatory composition comprising:
   a. a nucleic acid molecule having at least 89% sequence homology with the sequence of SEQ ID NO: 1 and at least 200 CpG dinucleotides; and
   b. a cationic liposome delivery vehicle.

5. The immunostimulatory composition of claim 4, wherein the nucleic acid molecule has at least 91% sequence homology with the sequence of SEQ ID NO: 1.

6. The immunostimulatory composition of claim 4, wherein the nucleic acid molecule comprises SEQ ID NO: 1.

7. The immunostimulatory composition of claim 4, wherein the liposome delivery vehicle comprises pairs of lipids selected from the group consisting of N-[1-(2,3-dioleyloxy)propyl]-N,N,N-trimethylammonium chloride (DOTMA) and cholesterol; N-[1-(2,3-dioleoyloxy)propyl]-N,N,N-trimethyl ammonium chloride (DOTAP) and cholesterol; 1-[2-(oleoyloxy)ethyl]-2-oleyl-3-(2-hydroxyethyl)imidazolinium chloride (DOTIM) and cholesterol; and dimethyldioctadecylammonium bromide (DDAB) and cholesterol.

8. A method of stimulating an immune response in a subject comprising administering to the subject the immunostimulatory composition of claim 4.

9. The method of claim 8, wherein the liposome delivery vehicle comprises lipids selected from the group consisting of multilamellar vesicle lipids and extruded lipids.

10. The method of claim 8, wherein the liposome delivery vehicle comprises pairs of lipids selected from the group consisting of N-[1-(2,3-dioleyloxy)propyl]-N,N,N-trimethylammonium chloride (DOTMA) and cholesterol; N-[1-(2,3-dioleoyloxy)propyl]-N,N,N-trimethylammonium chloride (DOTAP) and cholesterol; 1-[2-(oleoyloxy)ethyl]-2-oleyl-3-(2-hydroxyethyl)imidazolinium chloride (DOTIM) and cholesterol; and dimethyldioctadecylammonium bromide (DDAB) and cholesterol.

11. The method of claim 8, wherein administration is selected from the group consisting of intravenously, intramuscularly, intradermal, intraperitoneal, subcutaneously, by spray, by aerosol, in ovo, orally, intraocularly, intratracheally, and intranasally.

12. The method of claim 8, wherein the immunostimulatory composition further comprises a biological agent.

13. The method of claim 12, wherein the biological agent is selected from the group consisting of immune enhancer proteins, immunogens, vaccines, antimicrobials, and any combination thereof.

14. The method of claim 8, wherein the administration is before exposure to an infectious agent.

15. The method of claim 8, wherein the administration is after exposure to an infectious agent.

16. The method of claim 13, wherein the immune response stimulated is selected from the group consisting of a non-antigen specific immune response, an antigen specific immune response, an innate immune response, an adaptive immune response, a humoral immune response, a cell-mediated immune response, or a combination thereof.

17. The method of claim 8, wherein the subject is selected from the group consisting of mammal species, aquaculture species, and avian species.

18. The nucleic acid molecule of claim 1 having at least 260 CpG dinucleotides.

19. The nucleic acid of claim 1 having at least 280 CpG dinucleotides.

20. The nucleic acid molecule of claim 1 having 283 CpG dinucleotides.

* * * * *